US012290553B2

(12) United States Patent
Galabova et al.

(10) Patent No.: US 12,290,553 B2
(45) Date of Patent: May 6, 2025

(54) METHOD FOR VACCINATION AGAINST A SELF-ANTIGEN IN A HUMAN PATIENT

(71) Applicant: AC Immune SA, Lausanne (CH)

(72) Inventors: Gergana Galabova, Vienna (AT); Sabine Schmidhuber, Vienna (AT); Achim Schneeberger, Vienna (AT); Arne Von Bonin, Vienna (AT); Dorian Winter, Vienna (AT); Jana Zimmermann, Vienna (AT)

(73) Assignee: AC Immune SA, Lausanne (CH)

( * ) Notice: Subject to any disclaimer, the term of this patent is extended or adjusted under 35 U.S.C. 154(b) by 357 days.

(21) Appl. No.: 15/772,572

(22) PCT Filed: Nov. 2, 2016

(86) PCT No.: PCT/EP2016/076372
§ 371 (c)(1),
(2) Date: May 1, 2018

(87) PCT Pub. No.: WO2017/076873
PCT Pub. Date: May 11, 2017

(65) Prior Publication Data
US 2019/0091306 A1 Mar. 28, 2019

(30) Foreign Application Priority Data
Nov. 3, 2015 (EP) .................................... 15192794

(51) Int. Cl.
*A61P 25/16* (2006.01)
*A61K 39/00* (2006.01)
*A61P 37/06* (2006.01)

(52) U.S. Cl.
CPC ...... *A61K 39/0008* (2013.01); *A61K 39/0005* (2013.01); *A61K 39/0007* (2013.01); *A61P 25/16* (2018.01); *A61P 37/06* (2018.01); *A61K 2039/545* (2013.01); *A61K 2039/55505* (2013.01); *A61K 2039/577* (2013.01); *A61K 2039/6037* (2013.01); *A61K 2039/6081* (2013.01); *A61K 2039/627* (2013.01)

(58) Field of Classification Search
None
See application file for complete search history.

(56) References Cited

U.S. PATENT DOCUMENTS

| | | |
|---|---|---|
| 2011/0092434 A1 | 4/2011 | Mandler et al. |
| 2012/0269836 A1 | 10/2012 | Staffler et al. |
| 2014/0255435 A1 | 9/2014 | Staffler et al. |
| 2015/0306191 A1 | 10/2015 | Brunner et al. |

FOREIGN PATENT DOCUMENTS

| | | |
|---|---|---|
| CN | 1713817 A | 12/2005 |
| CN | 102573894 A | 7/2012 |
| CN | 102762206 A | 10/2012 |
| CN | 104427996 A | 3/2015 |
| CN | 104548089 A | 4/2015 |
| CN | 104685053 A | 6/2015 |
| JP | 2011-512363 A | 4/2011 |
| JP | 2012-533572 A | 12/2012 |
| JP | 2015-520739 A | 7/2015 |
| JP | 2015-528453 A | 9/2015 |
| WO | WO 2009/103105 A2 | 8/2009 |
| WO | WO 2011/009152 A1 | 1/2011 |
| WO | WO 2013/164355 A1 | 11/2013 |
| WO | WO 2014/033158 A2 | 3/2014 |

OTHER PUBLICATIONS

Schneeberger et al (Clin Invest 3: 1-4, 2013).*
Anderson (P Medscape, pp. 1-4, Aug. 1, 2014).*
Dolhun R, (Med Commun—MJFF Parkinson Res, pp. 1-32, Dec. 15, 2014).*
Landry et al (Vaccine 19: 399-402, 2001).*
Siegrist. C. (Section 1: Vaccine Immunol, pp. 1-26, 2008) (see submitted Pubmed abstract for publication date).*
Siegrist c General Aspects of Vaccination How do vaccines mediate protection: Abstract (for reference "X"), 2008.*
Nolz et al (Adv Exptl Med Biol 780, Ch 7, 69-83, 2011).*
Hendrikx et al, (Vaccine 27: 6530-6536, 2009).*
International Search Report and Written Opinion issued Feb. 15, 2017, in PCT/EP2016/076372, filed Nov. 2, 2016.
Extended European Search Report issued May 23, 2016, in Patent Application No. EP 15192794.4.
Affiris AG, "First Clinical Data of Therapeutic Parkinson's Disease Vaccine Encourages Continued Development", http://www.affiris.com/press_releases/PD01A_MJFF_E.pdf, XP002757397, retrieved on May 3, 2016, 2 pages.
Mandler, M. et al., "Active immunization against alpha-synuclein ameliorates the degenerative pathology and prevents demyelination in a model of multiple system atrophy", Molecular Neurodegeneration, vol. 10, No. 1, XP 021215331, Mar. 19, 2015, 15 pages.
Mandler, M. et al., "Next-generation active immunization approach for synucleinopathies: implications for Parkinson's disease clinical trials", Acta Neuropathologica, vol. 127, No. 6, XP 055203363, Feb. 14, 2014, pp. 861-879.
Paranjape, R. et al., "Is Prime Boost Strategy a Promising Approach in HIV Vaccine Development?", Journal of AIDS & Clinical Research, vol. 5, No. 4, XP 055270459, Jan. 1, 2014, 9 pages.

(Continued)

*Primary Examiner* — Daniel E Kolker
*Assistant Examiner* — Aditi Dutt
(74) *Attorney, Agent, or Firm* — Brian E. Davy; Bozicevic, Field & Francis LLP

(57) ABSTRACT

Disclosed is a method for vaccination against a self-antigen in a human patient wherein a dose with an effective amount of a self-antigen is administered to the patient to elicit a primary immune response, characterised in that the patient is subjected to a boost administration of said self-antigen, wherein the amount of the self-antigen in the dose for the boost administration is higher than the amount of the self-antigen in the dose used in the administration for the primary immune response.

10 Claims, 16 Drawing Sheets

Specification includes a Sequence Listing.

(56) References Cited

OTHER PUBLICATIONS

Morera, Y. et al., "Antigen dose escalation study of a VEGF-based therapeutic cancer vaccine in non human primates", Vaccine, vol. 30, No. 2, XP 028348287, Oct. 28, 2011, pp. 368-377.

Gonzales, G. et al., Therapeutic Vaccination with Epidermal Growth Factor (EGF) in Advanced Lung Cancer, Human Vaccines, vol. 3, No. 1, XP 008130590, Jan. 1, 2007, pp. 8-13.

Office Action issued Sep. 8, 2020 in corresponding Japanese Patent Application No. 2018-541534 (with English Translation), 18 pages.

Gergana Galabova et al., "Peptide-Based Anti-PCSK9 Vaccines—An Approach for Long-Term LDLc Management", PLOS ONE, vol. 9, No. 12, e114469, doi:10.1371/journal.pone.0114469, Dec. 4, 2014, pp. 1-18.

Combined Chinese Office Action and Search Report issued Feb. 3, 2021 in Chinese Patent Application No. 201680064233.5 (submitting English translation only), 19 pages.

"Tolerability and Safety of Subcutaneous Administration of Two Doses of Affitope® PD01A in Early Parkinson's Disease", Affiris AG, Clinicaltrials. Gov, Identifier: NCT01568099, Aug. 17, 2015, 6 pages.

"Follow-up Study to Assess One Boost Immunization with Affitope® PD01A with Regard to Safety and Clinical Activity (AFF008A)", Affiris AG, Clinicaltrials. Gov, Identifier: NCT02216188, Aug. 17, 2015, 6 pages.

Examination Report as received in the EP patent application No. 16 793 798.6-1110 dated Mar. 25, 2022, 12 pages.

Office Action as received in the corresponding JP patent application 2018-541534 dated Apr. 5, 2022, 8 pages.

Blum, et al, "A comparison of multiple regimens of pneumococcal polysaccharide-meningococcal outer membrane protein complex conjugate vaccine and pneumococcal polysaccharide vaccine in toddlers", vol. 18. No. 22, May 1, 2000, pp. 2359-2367.

Chaves, et al., "Improved anamnestic response among adolescents boosted with a higher dose of the hepatitis B vaccine", Vaccine 28 (2010), pp. 2860-2864.

Huebner, et al., "Long-term antibody levels and booster responses in South African children immunized with nonsvalent pneumococcal conjugate vaccine", Vaccine, Elsevier, Amsterdam, NL, vol. 22, No. 21-22. Jul. 29, 2004, pp. 2696-2700.

Hara, et al., "Immunogenicity and Safety after Booster Vaccination of Diphtheria, Tetanus, and Acellular Pertussis in Young Adults: an Open Randomized Controlled Trial in Japan", Clinical and Vaccine Immunology, vol. 20, No. 12. Dec. 2013, pp. 1799-1804.

Combined Chinese Office Action and Search Report issued Sep. 22, 2021 in Chinese Patent Application No. 201680064233.5 (submitting English translation only), 12 pages.

* cited by examiner

| Group | Number of Patients | Gender: Male (M)/ Female (F) | Age, Mean (SD); Min-Max | Time Since Diagnosis, months Mean (SD); Min-Max | Months Since Onset of Symptoms, Mean (SD); Min-Max | Hoehn & Yahr Stage Mean (SD); Min-Max |
|---|---|---|---|---|---|---|
| 15 µg – 15 µg | 4 | M: 3 F: 1 | 57.5 (9.81) 49 - 66 | 47.5 (20.38) 29 - 73 | 54.6 (16.56) 33 - 73 | 1.25 (0.5) 1 - 2 |
| 15 µg – 75 µg | 6 | M: 4 F: 2 | 57.8 (7.83) 50 - 68 | 63.2 (13.61) 39 - 76 | 66.7 (16.05) 41 - 85 | 0.83 (0.41) 0 - 1 |
| 75 µg – 15 µg | 6 | M: 2 F: 4 | 57.7 (7.20) 45 - 65 | 54.6 (16.82) 34 - 76 | 56.2 (16.08) 36 - 72 | 1.33 (0.52) 1 - 2 |
| 75 µg – 75 µg | 6 | M: 2 F: 4 | 55.0 (7.92) 47 - 67 | 56.3 (17.58) 33 - 77 | 67.9 (16.05) 37 - 82 | 1 (0) 1 |
| Untreated Group | 6 | M: 3 F: 3 | 57.0 (4.90) 49 - 63 | 47.4 (19.52) 32 - 81 | 50.5 (15.49) 34 - 71 | 1.42 (0.49) 1 - 2 |

| Groups | | AEs | | AEs by severity | | | Local | Systemic |
|---|---|---|---|---|---|---|---|---|
| | | | | Mild | Moderate | Severe | | |
| 15 µg - 15 µg | n | 19 | | 17 | 2 | 0 | 11 | 8 |
| | % | 16,1% | | 14,4% | 1,7% | 0,0% | 9,3% | 6,8% |
| 15 µg - 75 µg | n | 31 | | 21 | 10 | 0 | 20 | 11 |
| | % | 26,3% | | 17,8% | 8,5% | 0,0% | 16,9% | 9,3% |
| 75 µg - 15 µg | n | 26 | | 21 | 5 | 0 | 15 | 11 |
| | % | 22,0% | | 17,8% | 4,2% | 0,0% | 12,7% | 9,3% |
| 75 µg - 75 µg | n | 30 | | 22 | 6 | 2 | 19 | 11 |
| | % | 25,4% | | 18,6% | 5,1% | 1,7% | 16,1% | 9,3% |
| Untreated Group | n | 12 | | 10 | 2 | 0 | 0 | 12 |
| | % | 10,2% | | 8,5% | 1,7% | 0,0% | 0,0% | 10,2% |
| TOTAL | n | 118 | | 91 | 25 | 2 | 65 | 53 |
| | % | 100,0% | | 77,1% | 21,2% | 1,7% | 55,1% | 44,9% |

Fig. 7

| SOC_TERM | | Total | 15 µg - 15 µg | 15 µg - 75 µg | 75 µg - 15 µg | 75 µg - 75 µg | Untreated Group |
|---|---|---|---|---|---|---|---|
| General disorders and administration site conditions (1) | n | 67 | 13 | 19 | 16 | 19 | 0 |
| | % | 56,8% | 11,0% | 16,1% | 13,6% | 16,1% | 0,0% |
| Musculoskeletal and connective tissue disorders (2) | n | 9 | 3 | 2 | 1 | 1 | 2 |
| | % | 7,6% | 2,5% | 1,7% | 0,8% | 0,8% | 1,7% |
| Thereof local reactions | n | 65 (6+x(1) + 1x(2)) | 11 (11x(1)) | 20 (19x(1) + 1x(2)) | 15 (15x(1)) | 19 (19x(1)) | 0 |
| | % | 54,2% | 9,3% | 16,1% | 12,7% | 16,1% | 0,0% |
| Infections and infestations | n | 10 | 1 | 4 | 2 | 2 | 1 |
| | % | 8,5% | 0,8% | 3,4% | 1,7% | 1,7% | 0,8% |
| Nervous system disorders | n | 9 | 1 | 3 | 1 | 2 | 2 |
| | % | 7,6% | 0,8% | 2,5% | 0,8% | 1,7% | 1,7% |
| Injury, poisoning and procedural complications | n | 8 | 1 | 1 | 2 | 3 | 1 |
| | % | 6,8% | 0,8% | 0,8% | 1,7% | 2,5% | 0,8% |
| Surgical and medical procedures | n | 4 | 0 | 0 | 2 | 0 | 2 |
| | % | 3,4% | 0,0% | 0,0% | 1,7% | 0,0% | 1,7% |
| Gastrointestinal disorders | n | 2 | 0 | 0 | 2 | 0 | 0 |
| | % | 1,7% | 0,0% | 0,0% | 1,7% | 0,0% | 0,0% |
| Investigations | n | 2 | 0 | 1 | 0 | 1 | 0 |
| | % | 1,7% | 0,0% | 0,8% | 0,0% | 0,8% | 0,0% |
| Psychiatric disorders | n | 2 | 0 | 0 | 0 | 0 | 2 |
| | % | 1,7% | 0,0% | 0,0% | 0,0% | 0,0% | 1,7% |
| Respiratory, thoracic and mediastinal disorders | n | 2 | 0 | 1 | 0 | 1 | 0 |
| | % | 1,7% | 0,0% | 0,8% | 0,0% | 0,8% | 0,0% |
| Skin and subcutaneous tissue disorders | n | 2 | 0 | 0 | 0 | 1 | 1 |
| | % | 1,7% | 0,0% | 0,0% | 0,0% | 0,8% | 0,8% |
| Ear and labyrinth disorders | n | 1 | 0 | 0 | 0 | 0 | 1 |
| | % | 0,8% | 0,0% | 0,0% | 0,0% | 0,0% | 0,8% |
| Blood and lymphatic system disorders | | | | | | | |
| Cardiac disorders | | | | | | | |
| Endocrine disorders | n | 0 | 0 | 0 | 0 | 0 | 0 |
| Eye disorders | | | | | | | |
| Metabolism and nutrition disorders | % | 0,0% | 0,0% | 0,0% | 0,0% | 0,0% | 0,0% |
| Renal and urinary disorders | | | | | | | |
| Vascular disorders | | | | | | | |
| Total | n | 118 | 19 | 31 | 26 | 30 | 12 |
| | % | 100,0% | 16,1% | 26,3% | 22,0% | 25,4% | 10,2% |

Fig. 8

METHOD FOR VACCINATION AGAINST A SELF-ANTIGEN IN A HUMAN PATIENT

The present invention relates to a method for vaccination against a self-antigen in a human patient and sets of vaccine formulations suitable for such vaccinations.

Active Immunization using self-protein antigens consists of generating an immune response involving both T and B cells, which results in the induction of highly efficient B cell differentiation pathways through specific structures (germinal centers, GC) in which antigen specific B cells proliferate and differentiate into antibody-secreting plasma cells and memory B cells. Given the fact that autoimmunity is the major side effect of vaccines addressing self-proteins (for example Gilman et al., Neurology 64 (2005), 1553-1562), a potentially successful vaccine has to meet a series of criteria.

First, its antigenic component must not activate T cells but serve as a B cell antigen. Therefore, Ag needs to be presented by antigen-presenting cells on their MHC molecules. Binding to them requires the peptide Ags to (i) have a certain length (8-9 aa (amino acid residues) in case of MHC class I) and (ii) to exhibit defined aa residues in so called anchor positions (Rudolph, Ann. Rev. Immunol. 24 (2006), 419-466). In general, the antigenic epitope has to be short enough to prevent T cell activation but long enough to serve as an antibody epitope. However, the generation of an IgG type Ab response is also dependent on T helper (TH) cells, therefore, the vaccine must contain (an) epitope(s) capable of activating T helper (TH) cells. These must not be related to the Ag of interest as this could result in cellular autoimmunity. Ideally, they have to be strong TH epitopes and known to be incapable of activating Abs that crossreact with molecules/structures found in humans. In this respect, different protein carriers have been shown preclincally as well as clinically to be potent activators of T cell help. Keyhole Limpet Haemocyanin (KLH) is a well described "foreign to the human immune system" protein, generating powerful Ab responses when physically linked with specific antigenic epitopes, e.g. antigenic peptide sequences.

Tailoring the Ab response of a vaccine targeting a self-protein is the true challenge. It needs to tackle the desired structure without attacking related ones. This requires fulfilling two criteria at a time. One, the Abs raised need to bind the defined target, which is crucial for the vaccine's intended activity. Two, they must however not bind to related or homologous structures, which is an essential safety feature.

Parkinson's disease (PD) is the second most common neurodegenerative disorder. It is a complex, systemic disease eliciting a broad range of debilitating motor and non-motor symptoms. Typically, the presenting signs of PD are indefinite, non-motor symptoms including: neuropsychiatric (such as depression, REM sleep disorder), gastrointestinal (such as constipation) and autonomic disorders. The cardinal motor symptoms of PD include resting tremor, bradykinesia, rigidity and postural instability may begin up to a decade after the onset of its non-motor component. PD currently affects about 5 million people worldwide and its prevalence is rising as the global population ages.

Despite significant investment, there is currently no agent available with disease modifying properties. Treatments for PD primarily address motor symptoms through the use of dopaminergic strategies (levodopa or dopamine agonists, COMT- and MAO-B inhibitors), anticholinergic drugs, or deep brain stimulation, which are of symptomatic benefit only and are rife with side effects. Over 20 clinical trials with potential disease modifying agents have been performed or are currently ongoing; however, none of them has reached their clinical endpoints (AlDakheel et al., Neurotherapeutics 11, (2014) 6-23). Consequently, there is an urgent need for the development of novel, disease altering treatment strategies.

Increasing evidence points to a causal role of alpha synuclein (aSyn) oligomers in the processes that lead to neurodegeneration in PD. Lewy bodies or Lewy neurites are the histopathological signature markers of PD; they appear mainly in neurons and are predominantly composed of misfolded, fibrillar aSyn. Under physiological conditions, aSyn presents as a cytosolic, intracellular, unfolded protein enriched in the nucleus and in the pre-synaptic terminals; it has been suggested that aSyn might be physiologically involved with synaptic plasticity. In PD, pathological aggregated forms of aSyn, probably including oligomers of aSyn, seem to propagate Lewy body pathology, as well as the disease, by spreading from cell to cell in a prion-line manner. Furthermore, several lines of evidence in animal models support the theory that reducing accumulations of oligomeric aSyn may have disease-modifying effects (Games et al., Am. J. Pathol. 182 (2013), 940; Kim et al., J. Neurochem. 107 (2008), 303; Recasens et al., Ann. Neurol. 75 (2014), 351; and Winner et al., J. Neurosci. 32 (2012), 16906). Therefore, a treatment that reduces aSyn aggregates is acknowledged to have the potential to hinder disease progression (Lee et al., Neurosci. Res. 70 (2011), 339; Valera et al., Pharmacol. Ther. 138 (2013), 311). Significant progress has been made in the past decade towards developing immunotherapeutic approaches for clearing aSyn aggregates. Immunization strategies against aSyn have already been shown to promote the degradation of aSyn aggregates (Masliah et al., Neuron. 46 (2005), 857), prevent cell-to-cell transmission (Bae et al., J. Neurosci. 32 (2012), 13454; Benner et al., PNAS 101 (2004), 9435; Games et al., J. Neurosci. 34 (2014), 9441), and to reduce behavioural deficits (Masliah et al., PLoS One. 6 (2011), e19338) in animal models. Combined, these studies provide evidence that immunization against aSyn might have disease altering properties in humans.

AFFITOPE® PD01A was developed for the treatment of synucleinopathies such as PD (see: AFFiRiS press release reporting first clinical data on PD01A). PD01A is a peptide-KLH conjugate where the peptide moiety mimics the c-terminal region of human aSyn (WO 2009/103105 A2). It targets aSyn while avoiding closely relatedly protein family members including β-Synuclein (bSyn), which may have neuroprotective properties (Vigneswara et al., PLOS One 8 (2013), e61442). Increasing evidence points to a causal role of alpha-synuclein (aSyn) oligomers in the processes that lead to neurodegeneration in PD. Lewy bodies or Lewy neurites are the histopathological signature markers of PD; they appear mainly in neurons and are predominantly composed of misfolded, fibrillar aSyn. Furthermore, several lines of evidence in animal models support the theory that reducing accumulations of oligomeric aSyn may have disease-modifying effects. Therefore, a treatment that reduces aSyn aggregates might have the potential to hinder disease progression.

It was recently shown that vaccination with PD01A resulted in the decreased accumulation of aSyn oligomers and improved memory and motor defects in two mouse models of synucleopathies covering PD and MSA (multiple system atrophy) (Mandler et al., Acta Neuropathol. 127 (2014), 861; Mandler et al., Molecular Neurodegeneration 10 (2015), 10). Despite significant clinical investments, there is currently no therapeutically active agent available with disease modifying properties in humans. Treatments for PD primarily address motor symptoms through the use of dopaminergic strategies, anticholinergic drugs, or deep brain stimulation, which are of symptomatic benefit only and are rife with side effects. Over 20 clinical trials with potential disease modifying agents have been performed or are currently ongoing; however, none of them has reached their clinical endpoints. Consequently, there is an urgent need for the development of novel, disease altering treatment strategies.

It is an object of the present invention to provide more efficient, disease altering treatment strategies on the basis of immunization with self-antigens.

Therefore, the present invention provides a method for vaccination against a self-antigen in a human patient wherein a dose of an effective amount of a self-antigen is administered to the patient to elicit a primary immune response, characterised in that the patient is subjected to a boost administration of said self-antigen, wherein the amount of the self-antigen in the dose for the boost administration is higher than the amount of the self-antigen in the dose used in the administration for the primary immune response (i.e. higher than the amount of the self-antigen in the dose used for priming of the immune response).

Within the course of the present invention clinical data has been obtained by the applicant showing that in the process of vaccination of patients against self-antigens, boost administration plays a central role in obtaining effective immunological and therapeutical effects. It also turned out that data obtained with usual (non-self-antigens, such as pathogen antigens) are not comparable or congruent with vaccination strategies against self-antigens. The results obtained with the present application shows that it is advantageous if primary immunization (i.e. obtaining a primary immune response) is elicited with a relatively small amount of antigen and boost immunization is elicited with an amount of self-antigen is higher than in the administration for the primary immune response.

Despite promising first results in the course of the AFF008 trial (see press release, above), it was surprising that specific choice of the booster vaccination scheme according to the present invention was significantly triggering the clinical outcome of the overall performance of the various dosage regimen applied. Specifically in the long term, the dosage of the vaccine in the boosting phase (relative to the priming phase) was paramount for the specific antibody response and specific reactivity of the vaccine. This was specifically surprising, since the advantageous results are obtained when the amount of the self-antigen in the dose for the boost administration is higher than the amount of the self-antigen in the dose used in the administration for the primary immune response. This was neither derivable from the prior art suggesting vaccination against such antigens (e.g. WO 2009/103105 A2, WO 2011/009152 A1, WO 2014/033158 A2, etc.) nor from scientific reports on mouse models applying such vaccines (Mandler et al., Mol. Neurodeg. 10 (2015): 10; Mandler et al., Acta Neuropathol. 127 (2014): 861-879). This was even more unpredictable from the prior art, since the effect of the priming and booster doses as reported previously was regarded as being specific for the particular vaccine and for particular doses or even for particular individuals (e.g. Shete et al., J. Aids & Clin. Res. 5 (2014), DOI: 10.4172/2155-6113.1000293; Morera et al., Vaccine 30 (2012): 368-377; Gonzales et al., Hum. Vaccines 3 (2007): 8-13), but not for the class of self-antigen vaccines according to the present invention, especially for the self-antigens as specifically disclosed herein and shown in the example section of the present invention, namely Amyloid-beta, proprotein convertase subtilisin/kexin type 9 (PCSK9), membrane-bound immunoglobulins of the IgE type, huntingtin protein, CD26 or alpha synuclein (see below). It is essential for the present invention that the dose per administration for the primary immune response is low, i.e. lower than in the boost administration, so that the most specific B cells can be selected in this primary stage of vaccination. This strategy prevents the elicitation of less specific B cells and antigen receptors. On the other hand, the boost administration should be performed with high dosages (i.e. higher than in the primary immune response) concerning the amount of antigen to address as many B cells (created with the primary immune response) as possible, regardless where their current location is (bone marrow, lymph nodes, spleen, etc.). The higher amount used according to the present invention thereby enables a boost which is able to establish (based on the most specific B cells primed with the primary immune response) an efficient immunization against the self-antigen and, finally, an efficient control of this self-antigen by the present vaccination approach. In this connection it is also important to note that elicitation of the primary immune response may be achieved by one or more administrations of the primary dose of self-antigen to an individual to be vaccinated. Preferably, the primary immune response is elicited with two, more preferred with three, especially with four, administrations of the self-antigen. These administrations for primary immune response are preferably administered within time intervals of at least two, more preferred at least three, especially at least four weeks. Many vaccination schemes apply a bi-weekly or monthly vaccination interval which are therefore specifically preferred. The same holds true for the boost administration; as already stated, it is the dosage per administration, not the (total) amount of all doses administered that is the essential element for achieving the aims of the present invention, namely to elicit an overall efficient immune response with respect to a self-antigen.

This has been specifically shown for the present invention in a clinical trial concerning a vaccination strategy against PD targeting alpha synuclein ("aSyn") as a self-antigen by means of aSyn mimotopes to modulate the cerebral level of aSyn aggregates, the pathologic protein aggregates in the case of PD.

The applicant of the present invention has recently completed a first-in-humans phase I clinical trial assessing the safety and tolerability of two doses (15 µg and 75 µg) of a therapeutic vaccine, AFFITOPE® PD01A, administered to early PD patients. All adverse events were mild or moderate in severity and treatments were considered well tolerated. It was demonstrated that antigen (PD01A) administration (applied 4 times monthly) elicits an extrafollicular response that results in the appearance of (low) IgG Abs reacting with (i) PD01A, the peptide component of the vaccine as well as (ii) the targeted aSyn peptide sequence (FIG. 1). As B cells proliferate in germinal centers and differentiate into plasma cells, IgG Ab titers increase up to a peak value, reached 4 weeks after the third immunization (V8).

In order to better understand the induction of functional Abs e.g. aSyn-specific Abs through immunization, the relationship between the dose at the timepoint of priming immunization(s) and the resulting Ab response, as well as in how far a priming immune response (PD01A-induced response) to a self-antigen (e.g. aSyn) can be "reactivated" in humans, PD01A treated patients of the AFF008 study were analysed in a second clinical trial. To this end PD01A-immunized PD patients were boosted after 115 weeks (on average) with either one dose of 15 µg or 75 µg PD01A. In the AFF08A trial "Booster" exposure to antigen, PD01A, reactivates immune memory and results in a rapid increase of Ab titers against PD01A and the targeted aSyn peptide sequence (see FIG. 1), demonstrating a real secondary immune response. In general, short-lived plasma cells maintain peak Ab levels during a few weeks—after which serum Ab titers decline initially with the same rapid kinetics as following primary immunization. Long-lived plasma cells that have reached survival niches in the bone marrow continue to produce antigen-specific Abs, which then decline with slower kinetics.

Numerous determinants modulate the intensity of vaccine-induced GCs and thus of peak Ab responses. The main determinants are the nature of the vaccine antigen and its intrinsic immunogenicity.

Another important factor of primary vaccine Ab responses is the use of an optimal dose of vaccine antigen, which may be determined experimentally. As a rule, higher doses of antigen—up to a certain threshold—elicit higher primary Ab responses. Above the threshold dose, bell-shaped or plateau-type of responses may be seen. This may be particularly useful when immunocompetence is limited A limiting dose of vaccine may restrict primary immune responses but increases B cell competition for follicular dendritic cells-associated antigens, and thus result into a more stringent selection of higher affinity GC-B cells and into stronger secondary "boost" responses. Thus, in humans only specific combinations of antigen doses, e.g. an optimal antigenic dosing-window, at the "priming" phase and again in the "boosting" phase will provide a sufficient Ab response being able to modulate the expression of pathologic protein aggregates, e.g. aSyn aggregates in the case of PD.

As already stated above, the vaccine according to the present invention fulfils the relevant criteria as an appropriate vaccine addressing a self-antigen ("self-protein") which is directed to an antigen that is "self" to the vaccinated individual but must not—when administered—lead to autoimmunity as a side effect. Accordingly, the antigenic component of the self-antigen must not activate T cells but serve as a B cell antigen. Therefore, the antigen needs to be presented by antigen-presenting cells on their MHC molecules. Also the necessities reported by Rudolph, Ann. Rev. Immunol. 24 (2006), 419-466, apply. In general, the antigenic epitope has to be short enough to prevent T cell activation but long enough to serve as an antibody epitope. Moreover, the generation of an IgG type antibody response is also dependent on T helper (TH) cells, therefore, the vaccine must contain (an) epitope(s) capable of activating T helper (Th) cells (not related to the antigen of interest (to prevent cellular autoimmunity)). Ideally, the vaccines according to the present invention are strong Th epitopes and known to be incapable of activating antibodies that cross-react with other] molecules/structures found in humans. Accordingly, (protein) carriers, such as Keyhole Limpet Haemocyanin (KLH), have been shown preclincally as well as clinically to be potent activators of T cell help. KLH, for example, is a well described "foreign to the human immune system" protein, generating powerful Ab responses when physically linked with specific antigenic epitopes, e.g. antigenic peptide sequences. The immune response of the present vaccine needs to address the desired structure without attacking related ones. Accordingly, the antibodies raised in the vaccinated individual need to bind the defined target (the self-antigen), which is crucial for the vaccine's intended activity; moreover, these vaccine-elicited antibodies must not bind to related or homologous structures (as an essential safety feature).

Preferably, the self-antigens according to the present invention are those antigens that have been reported or suggested as scientifically plausible vaccine candidates or vaccination targets in the present field.

The method according to the present invention is therefore in principle applicable for all types of self-antigen vaccination strategies; however, it is preferred to apply the present method for self-antigens which are known to be problematic in obtaining efficient immune response. Accordingly, preferred self-antigens according to the present invention are selected from the group consisting of Amyloid-beta, proprotein convertase subtilisin/kexin type 9 (PCSK9), membrane-bound immunoglobulins of the IgE type, huntingtin protein, CD26 and an alpha synuclein antigen, preferably an alpha synuclein antigen, especially an alpha synuclein antigen containing the epitope DMPVDPDN and/or KNEEGAP.

It has been shown that if variations of the native sequence of the self-antigens are applied that have at least the same (preferably improved) immunization characteristics compared to the native sequence, immunization by vaccination may be further improved. Accordingly, it is clear that for the present invention such variations of the native self-antigen amino acid sequence are to be included within the term "self-antigen" according to the present invention as long as the immunization characteristics with respect to eliciting specific (native) self-antigen binding antibodies in the vaccinated individual is (at least) preserved (or, preferably, improved). Such variations may be provided by the AFFITOME® technology (e.g. disclosed in Schneeberger et al. Human Vacc. 6 (2010), 1-5). These variations provided by the AFFITOME® technology are termed AFFITOPE®s and are disclosed i.a. in WO 2004/062556 A and WO 2006/005707 A for Amyloid beta, in WO 2009/103105 A and WO 2011/020133 A for aSyn, in WO 2011/009152 A for AngII, in WO 2013/174920 A for C5a, in WO 2014/033158 A and in WO 2015/128287 A for PCSK9. The AFFITOPE®s disclosed in these documents are also preferred self-antigens according to the present invention.

Accordingly, it is preferred in the present invention to use a variation of a native sequence of a self-antigen as self-antigen, i.e. an AFFITOPE® (which may also be referred to as "mimotope" being a peptide that contains sequence variations compared with the original native sequence of the self-antigen, but which mimotope shows similar (the same or improved) immunization characteristics, i.e. is able to elicit an immune response that is similar or higher than the immune response that is obtained with the native sequence; a mimotope is therefore recognised by the same mAbs or pAbs as the native self-antigen but elicits a stronger immune response or an immune response that is not connected with severe adverse effects, such as neuro-inflammation). It is therefore preferred to use an alpha synuclein mimotope, an angiotensin II mimotope or a PCSK9 mimotope as self-antigens in the vaccination according to the present invention, more preferred an alpha synuclein mimotope selected from the group consisting of DQPVLPD (SEQ ID NO:3), DMPVLPD (SEQ ID NO:4), DSPVLPD (SEQ ID NO: 5), DSPVWAE (SEQ ID NO:6), DTPVLAE (SEQ ID NO:7) DQPVLPDN (SEQ ID NO: 8), DMPVLPDN (SEQ ID NO:9). DSPVLPDN (SEQ ID NO:10), DQPVTAEN (SEQ ID NO: 11), DSPVWAEN SEQ ID NO:12), DTPVLAEN (SEQ ID NO:13), HDRPVTPD (SEQ ID. NO: 14) DRPVTPD (SEQ ID NO: 15), DVPVLPD (SEQ ID. NO: 16), DTPVYPD (SEQ ID NO: 17), DTPVIPD (SEQ ID NO: 18), HDRPVTPDN (SEQ ID NO:19), DRPVTPDN (SEQ ID NO: 20), DNPVHPEN (SEQ ID NO:21), DVPVLPDN (SEQ ID NO:22), DTPVYPDN (SEQ ID. NO: 23), DTPVIPDN (SEQ ID. NO: 24), DQPVLPDG (SEQ ID NO: 25), DMPVLPDG SEQ ID NO:26), DSPVLPDG (SEQ ID NO: 27), DSPVWAEG SEQ ID NO:28), DRPVAPEG (SEQ ID NO:29) DHPVHPDS (SEQ ID NO:30), DMPVSPDR (SEQ ID NO: 31), DSPVPPDD (SEQ ID NO:32), DQPVYPDI (SEQ ID NO:33), DRPVYPDI (SEQ ID NO: 34), DHPVTPDR (SEQ ID NO:35), EYPVYPES (SEQ ID NO:36), DTPVLPDS (SEQ ID NO: 37), DMPVTPDT (SEQ ID NO: 38), DAPVTPDI (SEQ ID NO:39), DSPVVPDN (SEQ ID NO: 40), DLPVTPDR (SEQ ID NO:41), DSPVHPDT (SEQ ID NO:42), DAPVRPDS (SEQ ID NO: 43), DMPVWPDG (SEQ ID NO:44), DAPVYPDG (SEQ ID NO: 45), DRPVQPDR (SEQ ID. NO: 46), YDRPVQPDR (SEQ ID NO: 47), DMPVDPEN (SEQ ID. NO: 48) DMPVDADN (SEQ ID NO: 49), EMPVDPDN (SEQ ID NO:50), DNPVHPE (SEQ ID NO: 51), KNDEGAP (SEQ ID NO:52), ANEEGAP (SEQ ID NO: 53), KAEEGAP (SEQ ID NO: 54), KNAEGAP (SEQ ID NO: 55), RNEEGAP (SEQ ID NO: 56), HNEEGAP (SEQ ID NO: 57), KNEDGAP (SEQ ID NO:58), KQEEGAP (SEQ ID NO:59), KSEEGAP (SEQ ID NO: 60), KNDDGAP (SEQ ID NO:61), RNDEGAP (SEQ ID NO:62), RNEDGAP (SEQ ID NO: 63), RQEEGAP (SEQ ID NO:64), RSEEGAP (SEQ ID NO:65), ANDEGAP (SEQ ID NO: 66), ANEDGAP (SEQ ID NO: 67). HSEEGAP (SEQ ID NO: 68) ASEEGAP (SEQ ID NO: 69), HNEDGAP (SEQ ID NO: 70), HNDEGAP (SEQ ID NO:71), RNAEGAP (SEQ ID NO: 72), HNAEGAP (SEQ ID NO: 74), KSAEGAP (SEQ ID NO:75), KSDEGAP (SEQ ID NO: 76). KSEDGAP (SEQ ID NO:77), RQDEGAP (SEQ ID NO: 78), RQEDGAP (SEQ ID NO: 108), HSAEGAP (SEQ ID NO: 79), RSAEGAP (SEQ ID NO: 80), RSDEGAP (SEQ ID NO: 81), RSEDGAP (SEQ ID. NO: 82), HSDEGAP (SEQ ID NO: 83), HSEDGAP (SEQ ID NO: 84), and RQDDGAP (SEQ ID NO:85); especially DQPVLPD (SEQ ID NO:3), DSPVLPD (SEQ ID. NO: 3), DVPVLPD (SEQ ID NO:16), DSPVLPDG (SEQ ID NO:27), YDRPVQPDR (SEQ ID NO: 47), DHPVHPDS (SEQ ID NO:30), DAPVRPDS (SEQ ID. NO: 43) KNDEGAP (SEQ ID NO: 52) KQEEGAP (SEQ ID NO:59) or KSEEGAP (SEQ ID NO: 60); an angiotensin II mimotope selected from the group consisting of DPVYIHPF (SEQ ID NO:86) DAVYIHPF (SEQ ID NO: 87), DRHYIHPF (SEQ ID NO:88), DAAYIHPF (SEQ ID NO: 89) DRAYAHPF (SEQ ID NO:90), DPGYIHPF (SEQ ID NO:91), DRAYDHPF (SEQ ID NO:92), AAYIHPF (SEQ ID NO:93), RAYAHPF (SEQ ID NO:94), and PGYIHPF (SEQ ID NO:95), especially DRAYAHPF (SEQ ID NO: 92), RAYAHPF (SEQ ID NO: 94). DPGYIHPF (SEQ ID NO: 91) or PGYIHPF (SEQ ID NO:95); or a PCSK9 mimotope selected from the group consisting of SIPWSLERIT (SEQ ID NO:96), SIPWSLERITPPR (SEQ ID NO:97). SIPWSLERTTPPR (SEQ ID NO:98) VIPWNLERILPPR (SEQ ID NO:99) SVPWNLERIQPPR (SEQ ID NO:100), SIPWSLERTT (SEQ ID NO: 101), SIPWSLERLT (SEQ ID NO:102), SIPWSLERLTPPR (SEQ ID NO:103), SIPWSLERIQ (SEQ ID NO: 104) SIPWSLERIQPPR (SEQ ID NO:105), VIPWNLERIL (SEQ ID. NO: 106) and SVPWNLERIQ (SEQ ID NO.107), especially SIPWSLERIT (SEQ ID NO:96), VIPWNLERIL (SEQ ID NO: 106) or SVPWNLERIQ (SEQ ID NO:107).

It is preferred to use significantly higher amount of the self-antigen in the dose for the boost administration than in the dose for the primary immune elicitation. Accordingly, the amount of self-antigen in the dose for the boost administration is at least 20%, preferably at least 50%, more preferred at least 100%, especially at least 200%, higher than the amount used in the administration for the primary immune response.

In absolute amounts, it is preferred to use an amount of self-antigen in the dose for the boost administration of at least 20 µg, preferably at least 50 µg. In this connection it is important to note that the "µg self-antigen" referred to in the present invention refers to the amount of antigen peptide in the dose and does not include the carrier or linker part of the vaccine conjugate (if present).

For the present invention, it is important to administer the boost vaccination at a point in time when the primary immune response has already passed, i.e. when the antibody titers elicited with this primary vaccination (elicited by one, two, three, four or more vaccine administration(s) within the course of the primary immune response elicitation) have dropped beyond significant levels (e.g. beyond a given threshold level or even beyond detection limits of a (preferably rather insensitive) assay suitable for testing high numbers of samples) or have at least gone under 30%, preferably under 20%, especially under 10%, of the maximum antibody level being present in the course of the primary vaccination. Such levels may differ between different self-antigen vaccines but are usually present after at least 6 months after primary vaccination. Accordingly, the boost administration may—in a preferred embodiment—be administered at least 6 months, preferably at least 12 months, after the first administration of the self-antigen for eliciting the primary immune response. There may also be strategies where administering the boost is preferably performed at later points in time, for example 18 months, 2 years, three years or five years after the primary immune response vaccination.

Administration route according to the present invention are usually the same routes as for the current vaccination routes. Therefore, preferred administration of the self-antigen is subcutaneous, intradermal or intramuscular administration.

According to a preferred embodiment of the present invention, the self-antigen is administered together with an adjuvant, preferably aluminium oxyhydroxide. According to this most preferred embodiment, the current invention relates to the use of European Pharmacopoeial grade (Aluminium-oxyhydroxide, monograph 1664), more specifically to the product manufactured by Brenntag Biosector (2% Alhydrogel) tested towards EP compliance. Alhydrogel is available in three varieties: Alhydrogel 1.3%; Alhydrogel 2% and Alhydrogel "85". Alhydrogel 2% was elected as the International Standard Preparation for aluminium hydroxide gels. The pharmaceutical preparation according to the present invention is aseptically formulated into a suitable buffer, preferably an isotonic phosphate buffer (1 mM to 100 mM), preferably at a concentration of ≥1.0 mg/ml Alhydrogel (given as $Al_2O_3$ equivalent; this metric (Al as "$Al_2O_3$ equivalent") is used generally for the present invention; accordingly, all doses and amounts referred to in the present application, as far they are relating to aluminium oxyhydroxide refer to $Al_2O_3$ equivalents (of aluminium oxyhydroxide (Alhydrogel)), even more preferably at a concentration of ≥1.5 mg/ml Alhydrogel (given as $Al_2O_3$ equivalent), most preferable at a concentration of ≥2.0 mg/ml Alhydrogel (given as $Al_2O_3$ equivalent). The amount of aluminium salt for Alhydrogel is given as $Al_2O_3$ equivalent in line with the strength as stated by the manufacturer (i.e. 2% Alhydrogel equates to 2% $Al_2O_3$, i.e. 20 mg/mL). This concentration is directly convertible into the respective concentration of aluminium by using the respective molecular masses (20 mg/mL $Al_2O_3$ (Mw 101,96) corresponds to 10.6 mg/mL aluminium (molecular mass 26,98)).

Preferred self-antigens according to the present invention are polypeptides comprising 7 to 30, preferably 7 to 20, more preferably 7 to 16, most preferably 8, amino acid residues. It is also preferred (and often essential to get an immune response) to couple these peptide antigens to a pharmaceutically acceptable carrier, preferably a protein carrier, especially KLH (Keyhole Limpet Hemocyanin), Crm-197, tetanus toxoid (TT) or diphtheria toxin (DT).

According to a further preferred embodiment, the boost administration is repeated after some time, for example after one, two, three, five or ten years. Preferably, the second or further boosts are performed in the same or similar manner than the first boost administration, i.e. with the increased amount of self-antigen compared to the dose of the primary vaccination.

According to a further aspect, the present invention also relates to a kit for use in vaccination against a self-antigen in a human patient comprising
 a first vaccine formulation containing an effective amount of a self-antigen to elicit a primary immune response against the self-antigen, and
 a second vaccine formulation containing an effective amount of the self-antigen to elicit a boost immune response against the self-antigen,
wherein the amount of self-antigen in the second vaccine formulation is higher than in the first vaccine formulation.

In this kit, the vaccine formulation(s) according to the present invention (i.e. as disclosed herein) are provided.

The present invention also relates to the use of a kit according to the present invention for the manufacture of a vaccine for eliciting an immune response against a self-antigen in a human patient.

The present invention also provides a vaccine for use in vaccination of a human patient against a self-antigen wherein a dose with an effective amount of a self-antigen, especially a mimotope of a self-antigen, is administered to the patient to elicit a primary immune response, wherein the patient is subjected to a boost administration of said self-antigen, and wherein the amount of the self-antigen in the dose for the boost administration is higher than the amount of self-antigen in the dose used in the administration for the primary immune response.

The invention is further disclosed in the following examples and the figures, yet without being restricted thereto.

FIGS. 1A-D show injection of aSyn mimotope PD01A 20 months following priming leads to an immunological boost effect. (C) the most pronounced immunological effect is seen when priming was done with 4 monthly injections of 15 µg PD01A and boost was done with 75 µg PD01A. (D) A boost with 75 µg was still enhancing the antibody response over the level achieved during priming; FIGS. 1E-H show the aSyn specific antibodies in the human sera; FIGS. 1I-L show the KLH specific antibodies in the human sera.

FIGS. 2A-D show titers against AngII (3× bi-weekly vaccinations 5 µg and boost with 5 µg at week 22 and at week 33 with 50 µg).

FIG. 3 shows titers against huPCSK9 (long-term (3× bi-weekly vaccinations (two dosages) and 52 weeks follow-up); re-vaccination at week 52 with 30 µg).

FIG. 7 shows the AEs by study group of the AFF008A clinical trial.

FIG. 8 shows the AE's with SOC-term by study groups of the AFF008A clinical trial.

EXAMPLES

Example 1

PD Vaccination Boost

Figure 1A:
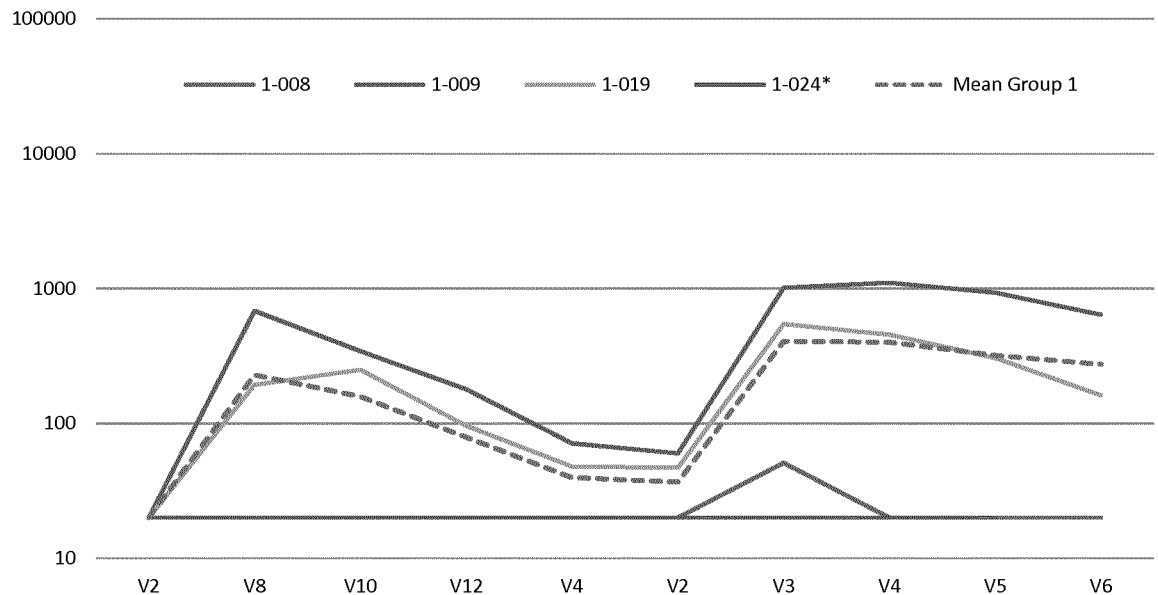
Figure 1B:
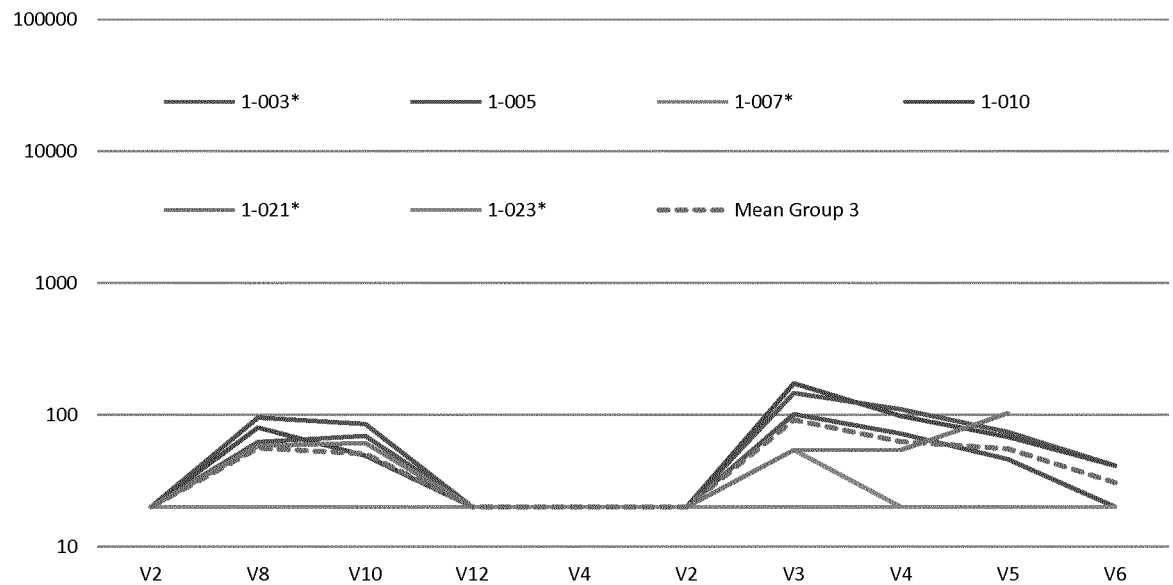
Figure 1C:
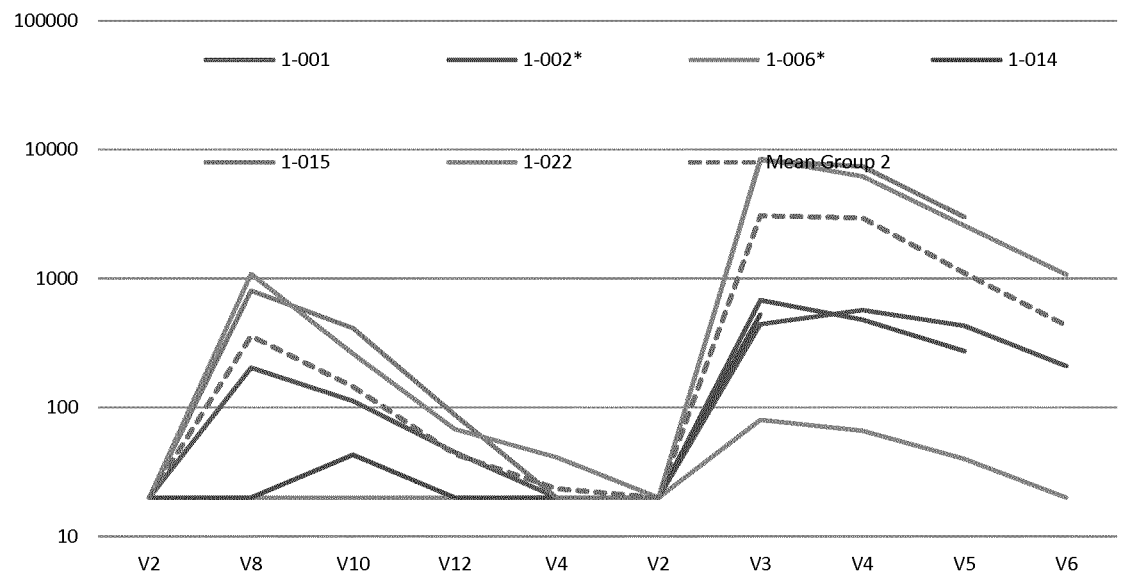
Figure 1D:
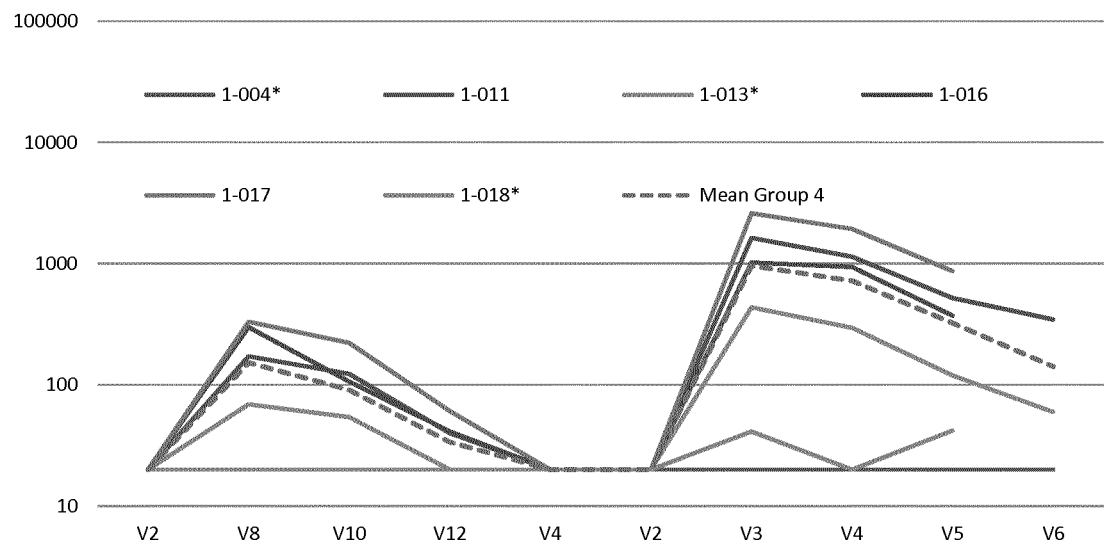
Figure 1E:
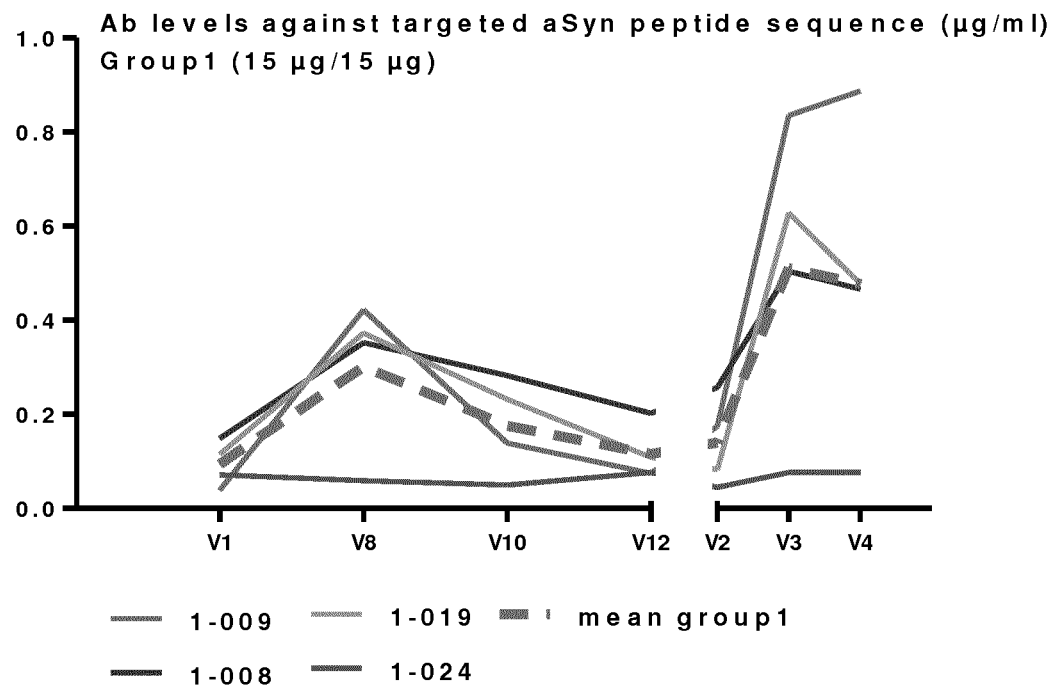
Figure 1F:
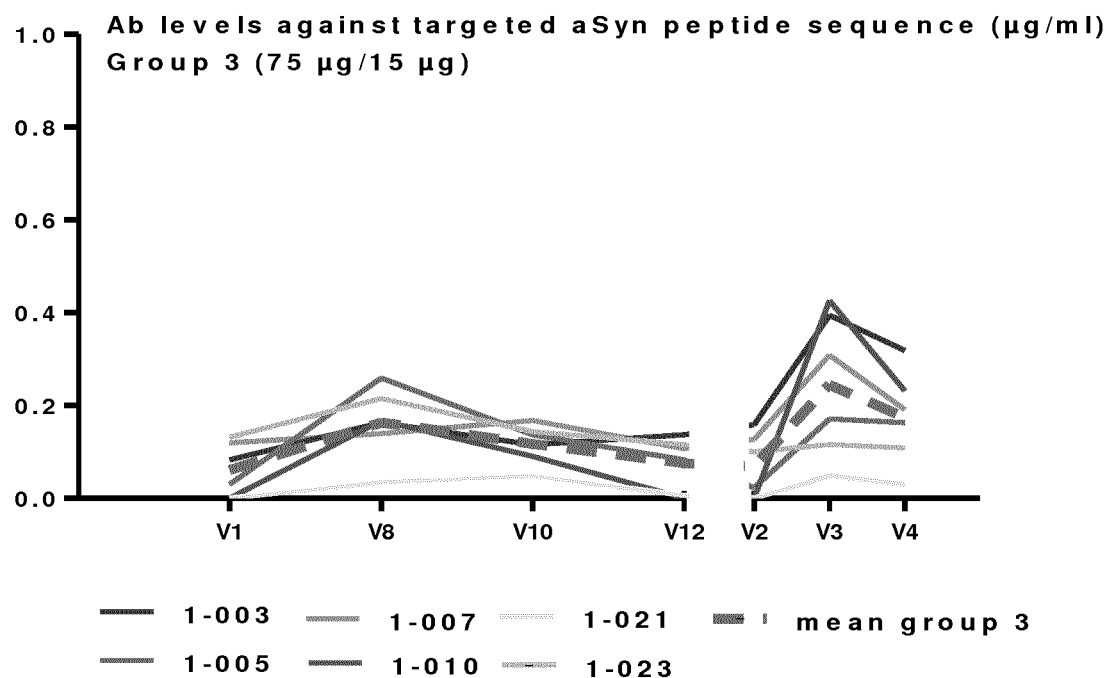
Figure 1G:
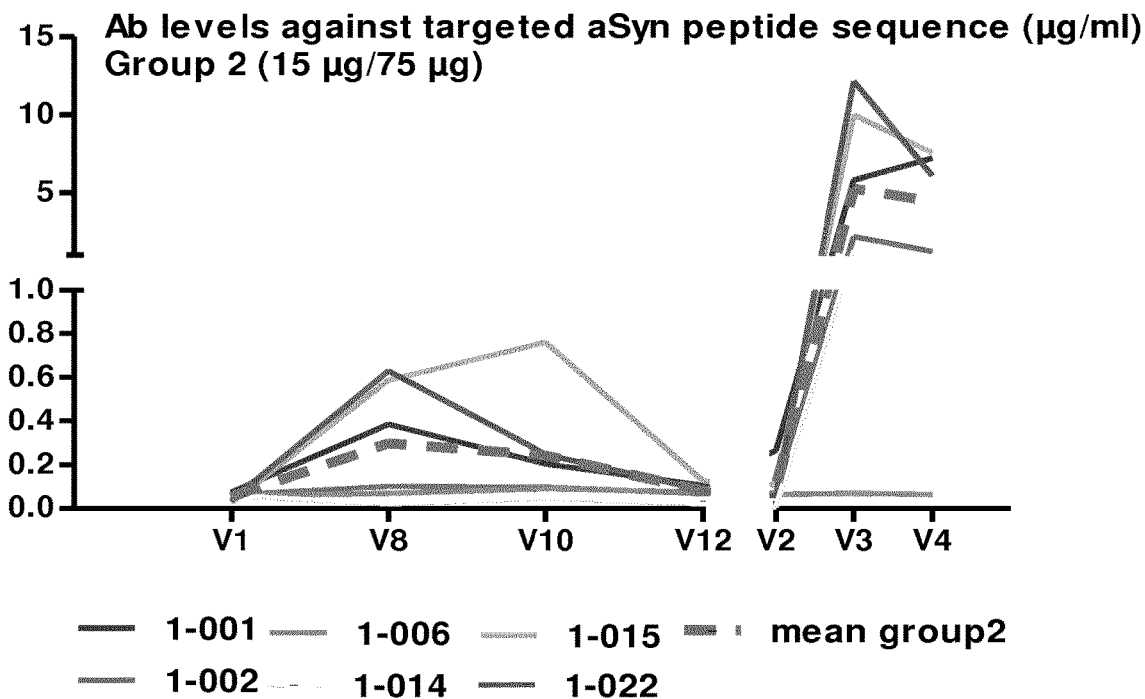
Figure 1H:
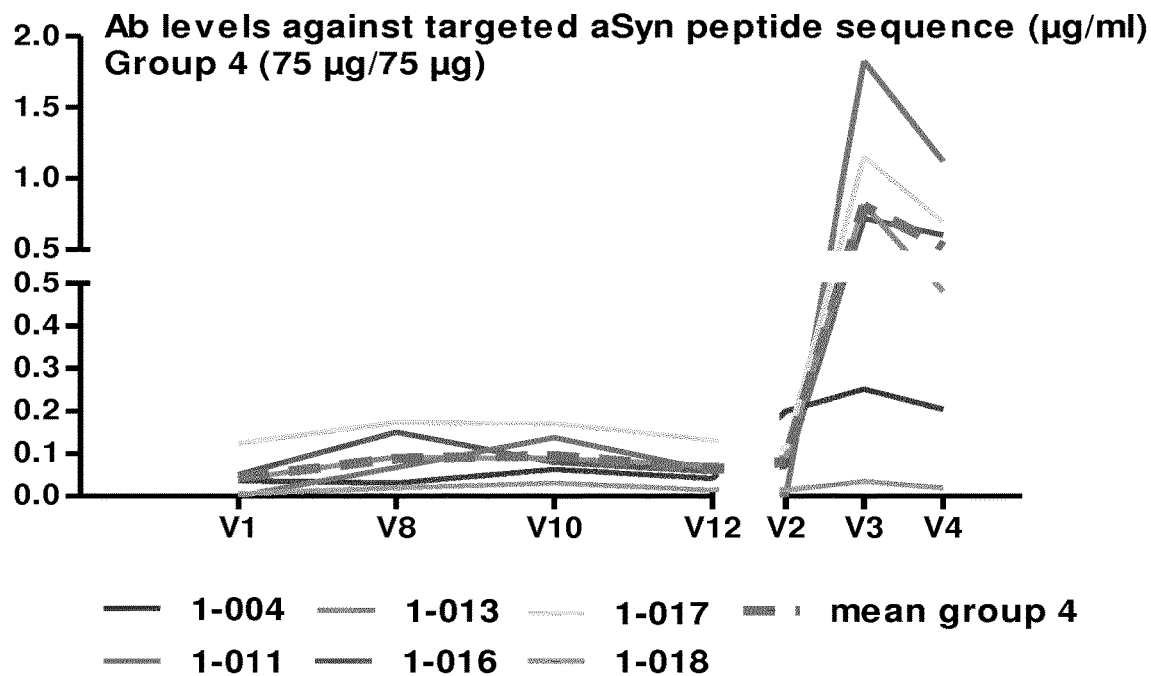
Figure 1I:
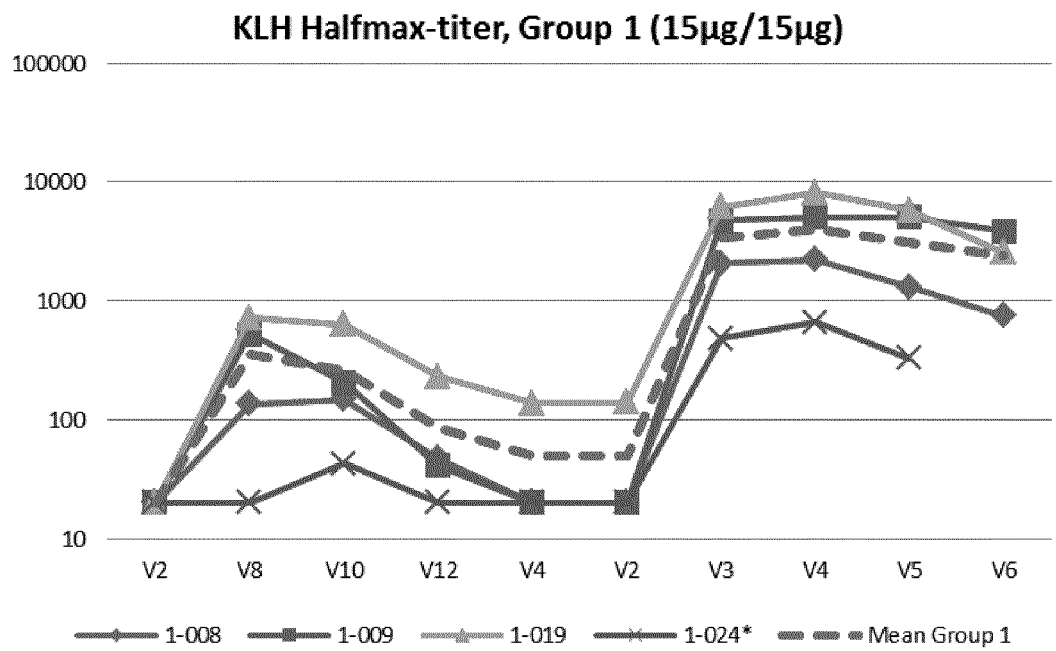
Figure 1J:
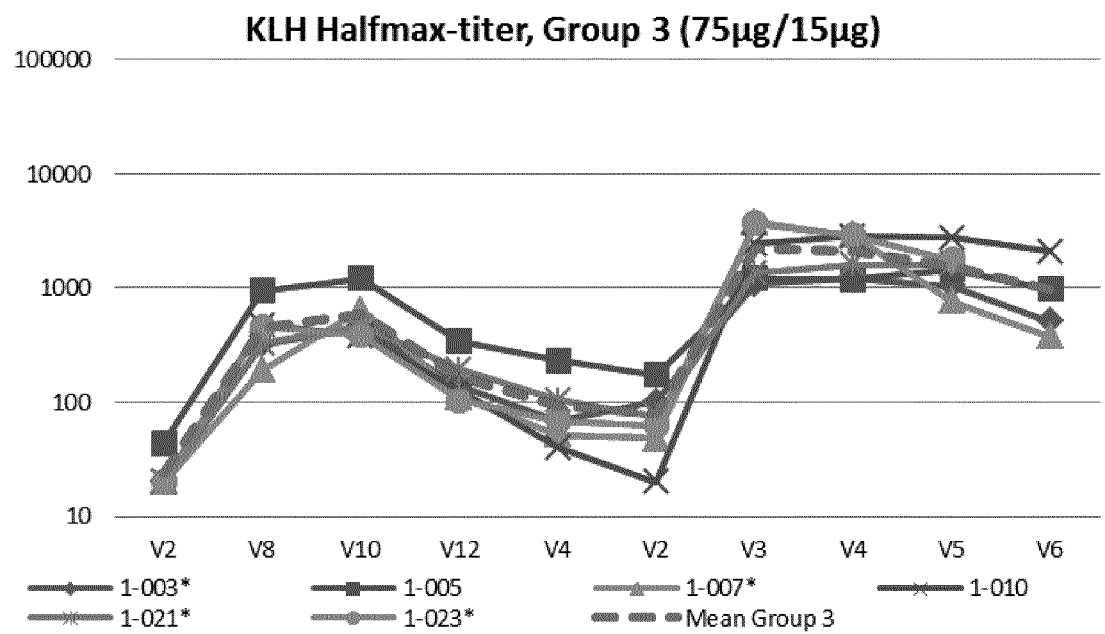
Figure 1K:
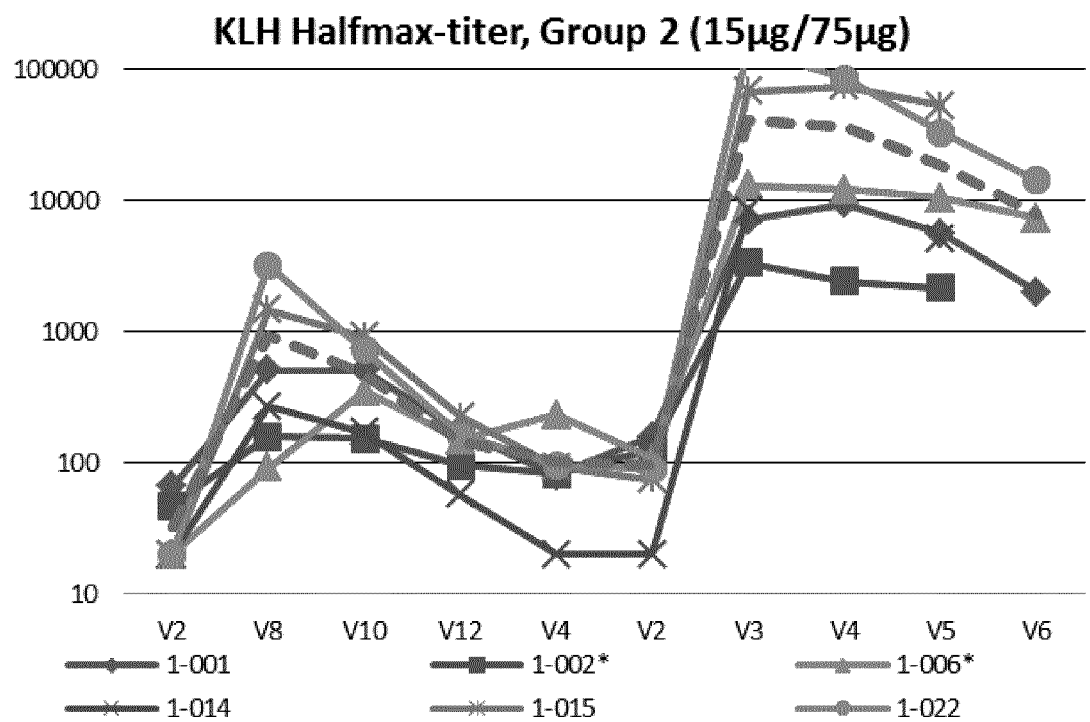
Figure 1L:
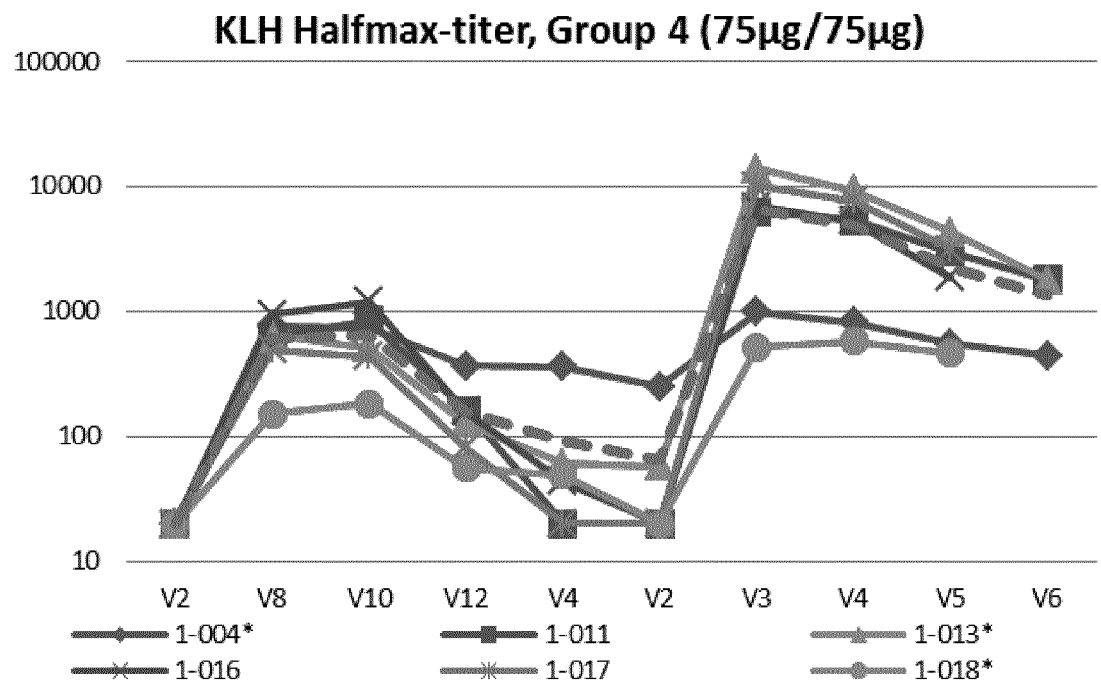
Figure 2A:
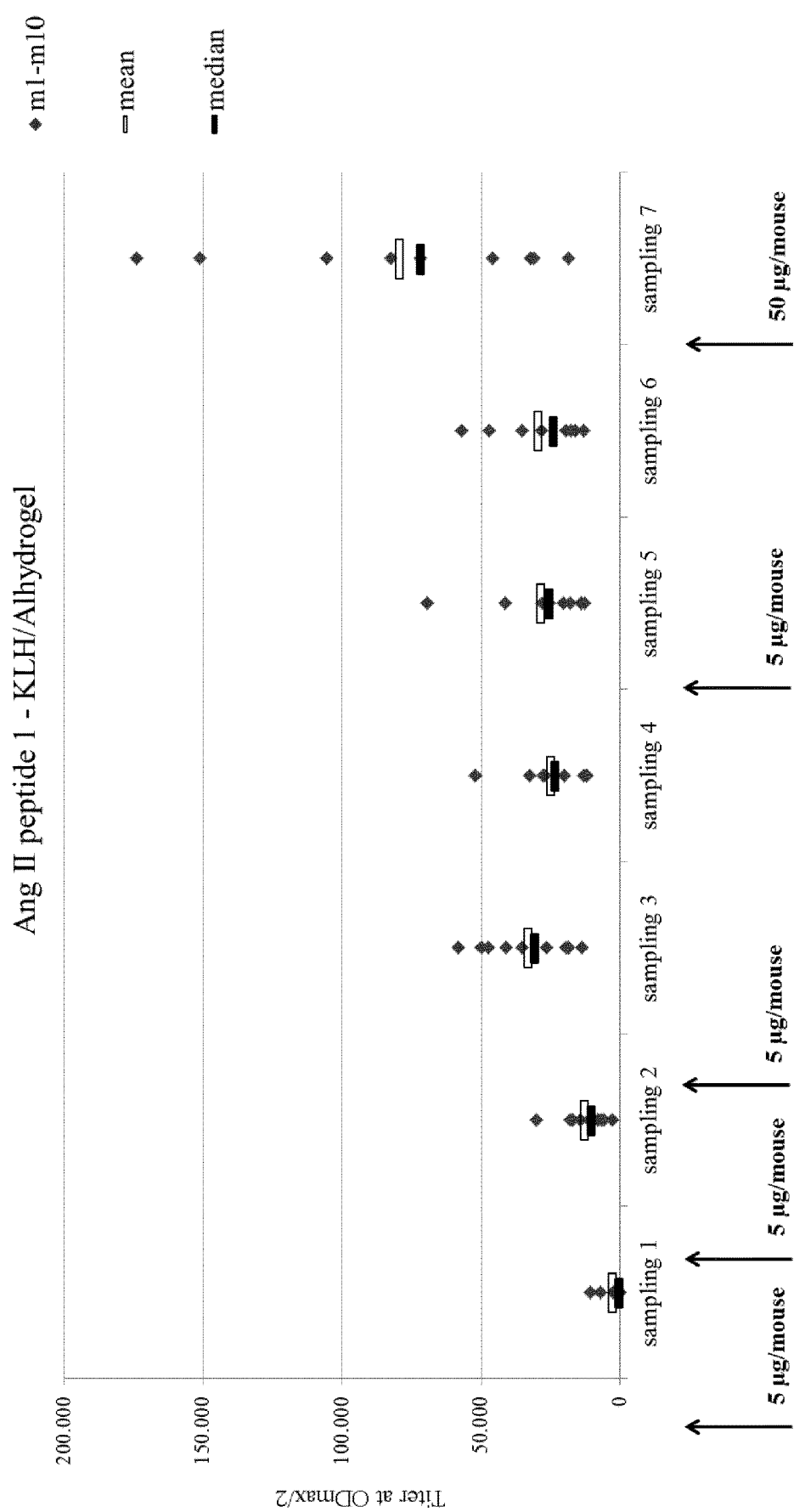
Figure 2B:
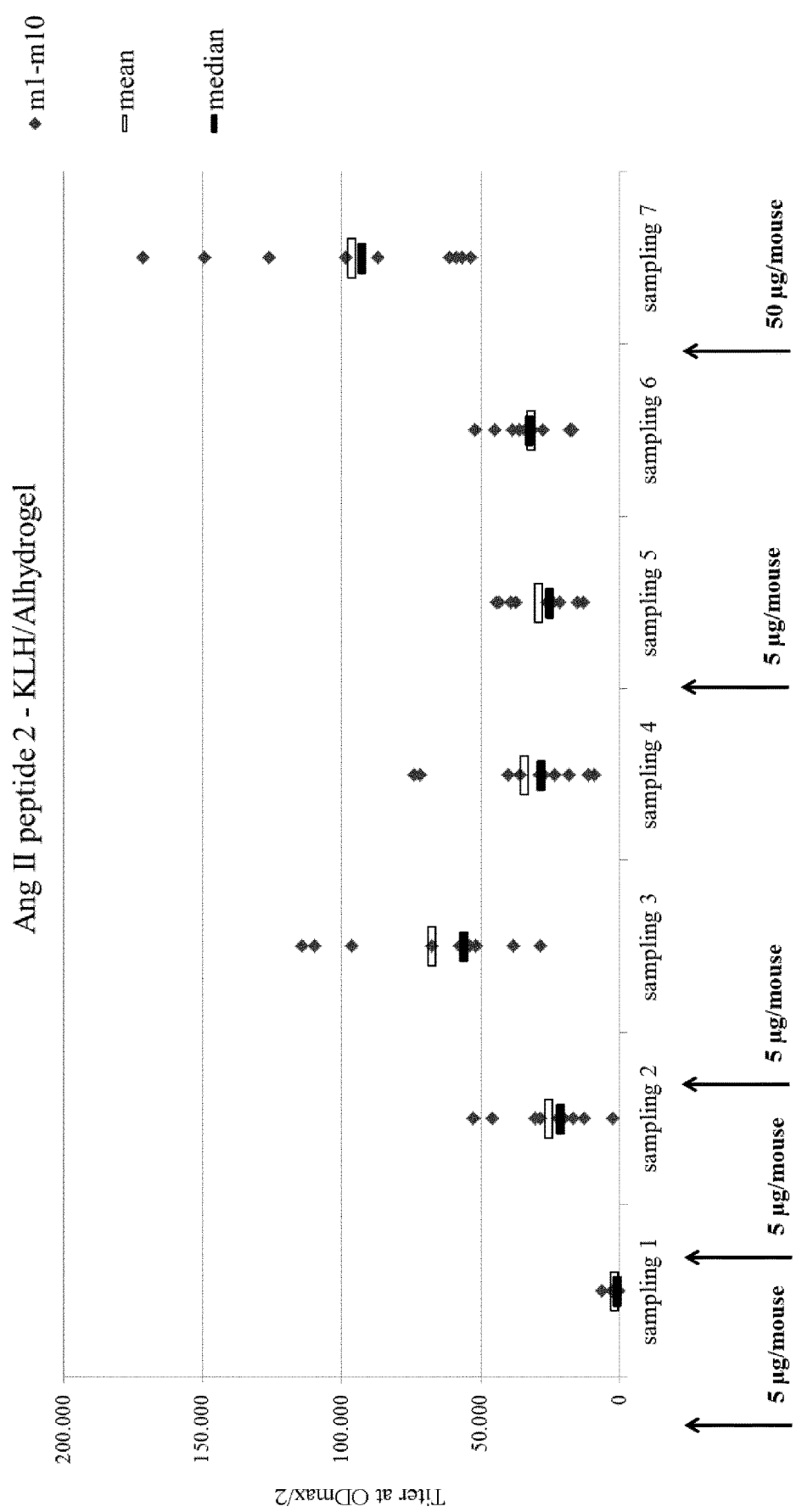
Figure 2C:
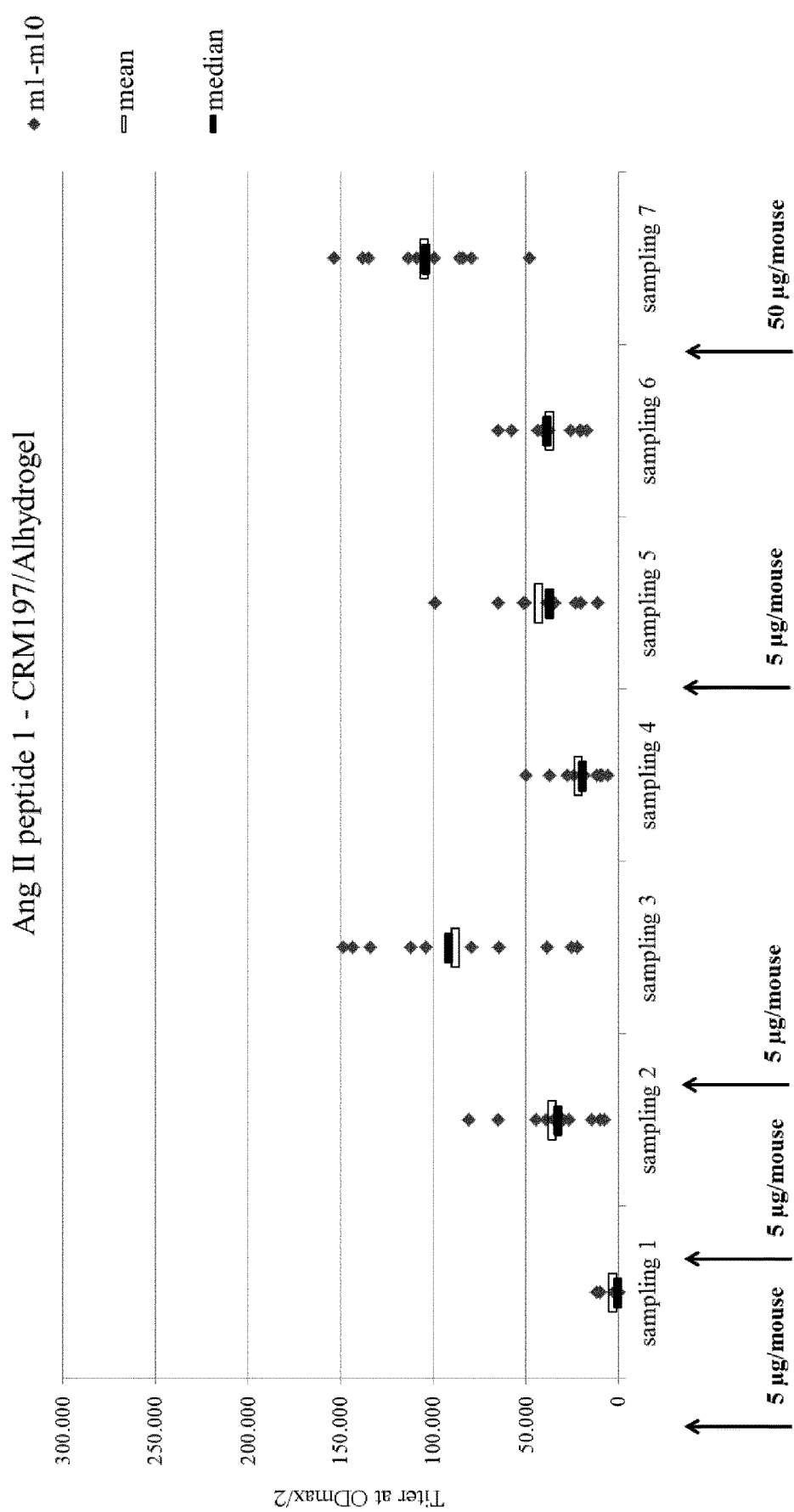
Figure 2D:
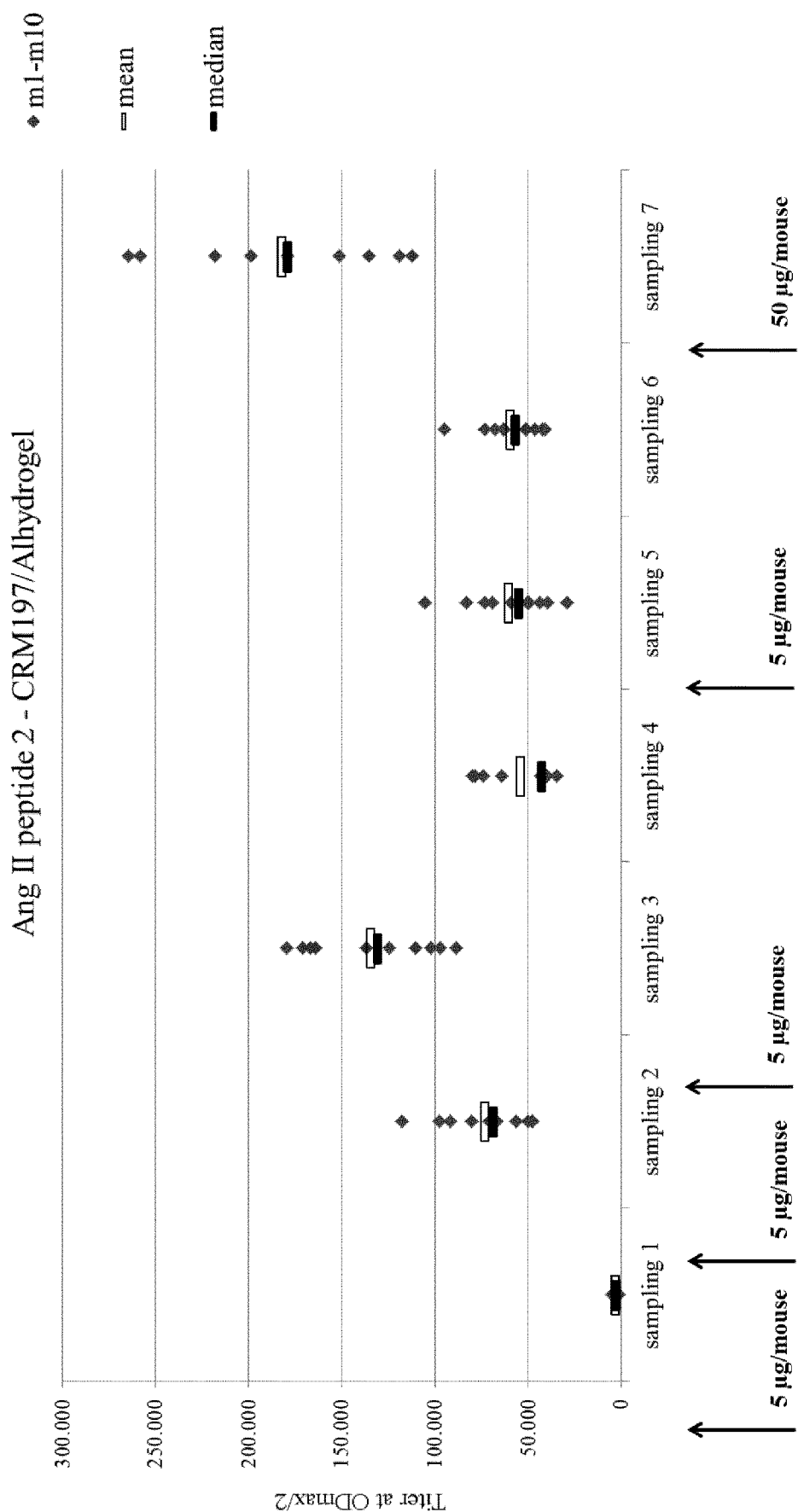

AFFITOPE® PD01A was developed for the treatment of synucleinopathies such as PD (WO 2009/103105 A2). PD01A is a peptide-KLH conjugate where the peptide moiety mimics the C-terminal region of human aSyn (with the native epitope DMPVDPDN). It targets aSyn while avoiding closely relatedly protein family members including β-Synuclein (bSyn), which may have neuroprotective properties (Vigneswara et al., PLoS One 8 (2013), e61442). It was recently shown that vaccination with PD01A resulted in the decreased accumulation of aSyn oligomers and improved memory and motor defects in two mouse models of PD (Mandler et al., Acta Neuropathol. 127 (2014), 861; Mandler et al., Molecular Neurodegeneration 10:10 (2015)).
Participants:

Trial participants were recruited from Vienna, Austria and surrounding areas. For inclusion in the clinical trial, patients had to have a confirmed diagnosis of PD. Individuals with idiopathic Parkinson's disease whose disease was known for less than 4 years and who presented in Hoehn & Yahr Stages I/II (Goetz et al., Mov. Disord. 19 (2004), 1020; Hoehn et al., Neurology 17 (1967), 427) and fulfilled the UK Parkinson's Disease Society Brain Bank Criteria (Hughes et al., J. Neurol. Neurosurg. Psychiatry 55 (1992), 181).

The results of Dopamine Transporter-Single Photon Emission Computed Tomography (DAT-SPECT) examination of the patient's brain and the magnetic resonance imaging (MRI) scan had to be consistent with the diagnosis of PD. All potential participants treated with conventional PD therapy must have had received stable doses for at least 3 months prior to the study period and the intention to continue during the entire trial period.

All study subjects provided voluntary informed consent. The trial protocol, patient information, informed consent and all other required trial documents were submitted to an independent ethics committee.
Materials and Methods:

AFFITOPE® PD01A was first applied to 24 individuals suffering from early PD in AFF008, a phase I clinical trial designed to primarily assess the safety and tolerability of the vaccine, and, in the second place, its immunological and clinical activity (explorative analysis). To this end, two doses (15 µg or 75 µg AFFITOPE® PD01A (i.e. 15 µg or 75 µg peptide C-DMPVDPDN coupled to the corresponding amount of KLH) adsorbed to 1 mg Alhydrogel (as $Al_2O_3$ equivalent)) were applied 4 times at 4-week intervals. Each dose was applied to 12 patients. In addition, up to 8 patients were offered participation within an untreated control group. Results obtained (i) confirmed the safety and tolerability of the vaccine, (ii) demonstrated the induction of a vaccine-specific IgG response, and, (iii) provided evidence in favour of the intended clinical activity. All 32 patients were offered a follow-up observation study (AFF008E), 31 (24 vaccine patients and 7 controls) accepted and finished the study. One patient of the low dose group was lost to follow-up. AFF008E participants were offered a single "boost injection" with a low (15 μg; derived from the high dose by bedside mixing) or high dose (75 μg) formulation resulting in 4 different treatment groups: low dose (AFF008)—low dose (AFF08A); low dose—high dose; high dose—low dose and high dose—high dose. Patients of the control group were left untreated. A total of 28 (22/6) accepted and all 28 finished the AFF008A study.

Injections were applied to the s.c. tissue by the principle investigator. All administrations were performed at the trial site. Patients in the treatment groups were randomized to receive 15 μg or 75 μg AFFITOPE® PD01A. Both formulations contain 0.5 mg aluminium equivalent.

The trials were performed in compliance with Good Clinical Practice (GCP), the Declaration of Helsinki with amendments (2013), and local legal and regulatory requirements (Austrian Drug Law) and applicable international regulations. The trial is registered on an approved clinical trial repository (identifiers: NCT01568099 NCT02216188).

The results are shown in FIGS. 1A-L. 1A-D show injection of aSyn mimotope PD01A 20 months following priming leads to an immunological boost effect. (C) the most pronounced immunological effect is seen when priming was done with 4 monthly injections of 15 μg PD01A and boost was done with 75 μg PD01A. (D) A boost with 75 μg was still enhancing the antibody response over the level achieved during priming.

FIGS. 1E-H show aSyn epitope response; FIGS. I-L show KLH response. All FIGS. 1A-L show antibody titers from human sera.

FIGS. 1E-H and FIGS. 1I-L are organized similarly to FIGS. 1A-D. Dotted red line represents group mean. Headline of the figures denotes vaccine doses: priming dose (AFF008)/boost dose (AFF008A). Groups sizes: n=4 (15 μg/15 μg), n=6 for all other groups. Time period covered on the figures: 3.5 years. Early Parkinson disease patients (defined by Hoehn and Yahr stages I/II) got 4 priming immunizations at doses of 15 or 75 μg at intervals of 28 days. Antibodies to the immunizing peptide (PD01), to the targeted alpha-synuclein epitope (aa110-130; formulated as a BSA conjugate) and to KLH were quantified by ELISA. Priming dose was instrumental primarily with regard to the longevity of the antibody response: the low dose triggered antibody responses that lasted longer than the high dose, the magnitude of both responses was comparable. Similarly, the outcome of the boost was determined by the doses: the low dose achieved a reactivation of the antibody response to the level of the priming response. The high dose by contrast enhanced the antibody response up to tenfold as compared to the response obtained during the priming phase. The best response, that forms the basis of the invention, was seen at the low dose high dose combination for priming and boost.

Example 2

AngII Vaccination Boost

Vaccines

The peptides DRAYAHPF, RAYAHPF, DPGYIHPF and PGYIHPF were conjugated via the heterobifunctional linker GMBS (4-Maleimidobutyric acid N-hydroxysuccinimide ester) to KLH (Keyhole Limpet Hemocyanin) or CRM197 (Cross Reactive Material 197). The indicated amounts of coupled peptides (1, 5, 30, 150 μg) were suspended with aluminium hydroxide (end concentration of aluminium hydroxide was 0.2%). As buffer, either PBS or mannitol/phosphate was used.

Animal Experiments

Female BALB/c mice were kept under a 12 h light/dark cycle and had access to food and water ad libitum. Age of mice at the beginning of experiments was around 8 to 10 weeks.

Per group, 10 Balb/c mice were subcutaneously immunized. Mice were initially injected three times in 2 week intervals with a volume of 1 ml in total (2×500 μl into the left and the right shoulder region). Blood was taken several times in regular intervals after the third injection. The data presented here is from plasma taken approximately 8 months after the third injection (indicated as P3i). Approximately 8.5 months after the third injection, half of the remaining mice in each group were boosted either with the same amount of antigen as in the first three immunisations or was immunised with higher/lower amounts, see scheme below. Final plasma (indicated as P4b) was taken 6 weeks after the fourth vaccination.

| General set-up: | | | |
|---|---|---|---|
| Vaccination no. 1/2/3 | No. of mice* | Vaccination no. 4 | Nr. of mice* |
| 1 μg coupled peptide | 10 | "low" = 1 μg coupled peptide | 5 |
| | | "high" = 30 μg coupled peptide | 5 |
| 30 μg coupled peptide | 10 | "low" = 1 μg coupled peptide | 5 |
| | | "high" = 30 μg coupled peptide | 5 |
| 150 μg coupled peptide | 10 | "low" = 5 μg coupled peptide | 5 |
| | | "high" = 150 μg coupled peptide | 5 |

*due to the duration of the experiment, some mice already died before the end of the experiment. Therefore, data from less mice are shown for certain groups.

For AngII peptide experiments, 10 Balb/c mice were injected subcutaneously according to the following table:

| | Peptide dose, injection volume | Time-point |
|---|---|---|
| 1st injection | 5 μg peptide, 200 μl | week 0 |
| Sampling 1 | — | week 2 |
| 2nd injection | 5 μg peptide, 200 μl | week 2 |
| Sampling 2 | — | week 4 |
| 3rd injection | 5 μg peptide, 200 μl | week 4 |
| Sampling 3 | — | week 6 |
| Sampling 4 | — | week 20 |
| 4th injection | 5 μg peptide, 200 μl | week 22 |
| Sampling 5 | — | week 24 |
| Sampling 6 | — | week 31 |
| 5th injection | 50 μg peptide, 200 μl | week 33 |
| Sampling 7 | — | week 35 |

Peptide ELISA

To determine the immunogenicity of the vaccines, 96-well Nunc-Maxisorb plates were coated with 1 μM of the respective injected peptides coupled to bovine serum albumin (BSA) in 0.1 M $NaHCO_3$, pH 9.2-9.4. Unspecific binding was blocked by incubation with blocking buffer (5% BSA in PBS). Appropriate serum dilutions were added to the wells, serially diluted 1:2 fold and incubated for approximately 1 hour at 37° C. Bound antibodies were detected by incubation with biotinylated goat anti-mouse IgG, followed by horseradish peroxidase coupled to Streptavidin. As substrate ABTS was added and the optical density (OD) at 405 nm was measured in a Microwell plate-reader. The titres were defined as the dilution of the serum where 50% of the $OD_{max}$ in the assay are reached.

To calculate the fold induction of antibodies after re-boost, anti-injected peptide titers of individual mice determined after the fourth immunisation were divided through the titers determined for ~8 months after the third immunisation. Mean factors obtained for each group are depicted in the graphs.

The results are shown in FIGS. 2A-D. Groups of BALB/c mice (n=10) received priming vaccinations at weeks 0, 2 and 4 by injecting 5 µg of Angiotensin II mimicking peptides coupled to KLH (A) and (B), of Angiotensin II mimicking peptides coupled to CRM (C) and (D). Immunization with either vaccine led to the elicitation of an Ang II specific IgG Ab response. All vaccines showed similar responses in terms of kinetics but differed to some extent with regard to magnitude. A boost with a low dose, i.e. 5 µg of the respective vaccine, applied at week 22 failed to significantly enhance the Ang II-specific Ab response, regardless of the vaccine type/formulation. By contrast, application of the respective vaccine at a high dose, i.e. 50 µg, at week 33 boosted the Ang II-specific Ab response clearly beyond the levels that had been reached during the priming phase.

Example 3

PCSK9 Vaccination Boost

Materials and Methods

Vaccine:
The peptides SIPWSLERIT, VIPWNLERIL and SVPWNLERIQ were conjugated via the heterobifunctional linker GMBS (4-Maleimidobutyric acid N-hydroxysuccinimide ester) to KLH (Keyhole Limpet Hemocyanin).

Animal Experiments:
5 BALB/c mice were subcutaneously immunized. Mice had access to food and water ad libitum and were kept under a 12 h light/dark cycle. The age of mice at the beginning of 21 experiments was 8 to 10 weeks. Mice were injected three times in 2 week intervals with either 5 µg or 25 µg of net peptide coupled to KLH and adsorbed to Alhydrogel as adjuvant in a volume of 1 ml in total. Blood was taken approximately 2 weeks after each injection and in a monthly interval after the final $3^{rd}$ immunization (for up to a year). At week 52 post prime immunization mice were re-vaccinated ($4^{th}$ immunization) with 25 µg of net peptide coupled to KLH and adsorbed to Alhydrogel as adjuvant in a volume of 1 ml in total. Blood was taken 2 and 4 weeks after the $4^{th}$ immunization (Plasma 4a and 4b, respectively).

Protein ELISA:
To determine the immunogenicity of the vaccines, and thus to identify the amount of PCSK9 specific antibodies in the plasma of immunized animals, ELISA immunoassay was performed. The ELISA immunoassay generates a signal which can be easily quantified and represents a quantitative measure of the amount of vaccine induced PCSK9-specific antibodies. Thus the titers as measured by ELISA correlate directly with the amount (µg/ml) of target specific antibodies in the plasma sample of treated animals. All plasma samples were collected two weeks after the final immunization and equality treated. In order to have a direct comparison, the quantitative evaluation by the PCSK9 Protein ELISA immunoassay of the vaccine induced PCSK9-specific antibodies and the comparison to their relative controls (originals sequence and negative control) was performed for all samples simultaneously. For this purpose, ELISA plates were coated with recombinantly expressed human PCSK9 protein. Unspecific binding was blocked by incubation with blocking buffer (1% BSA in PBS). Appropriate serum dilutions (pools with a starting dilution of 1:100) were added to the wells, serially diluted 1:2 fold (12 dilution steps) and incubated for approximately 1 hour. Bound antibodies were detected by incubation with anti-mouse IgG antibody, ABTS was added as substrate and the OD at 405 nm was measured. As negative control sera from the control group injected with an irrelevant peptide were analyzed. The titers were defined as the dilution of the serum where 50% of the $OD_{max}$ in the assay is reached.

Figure 3:
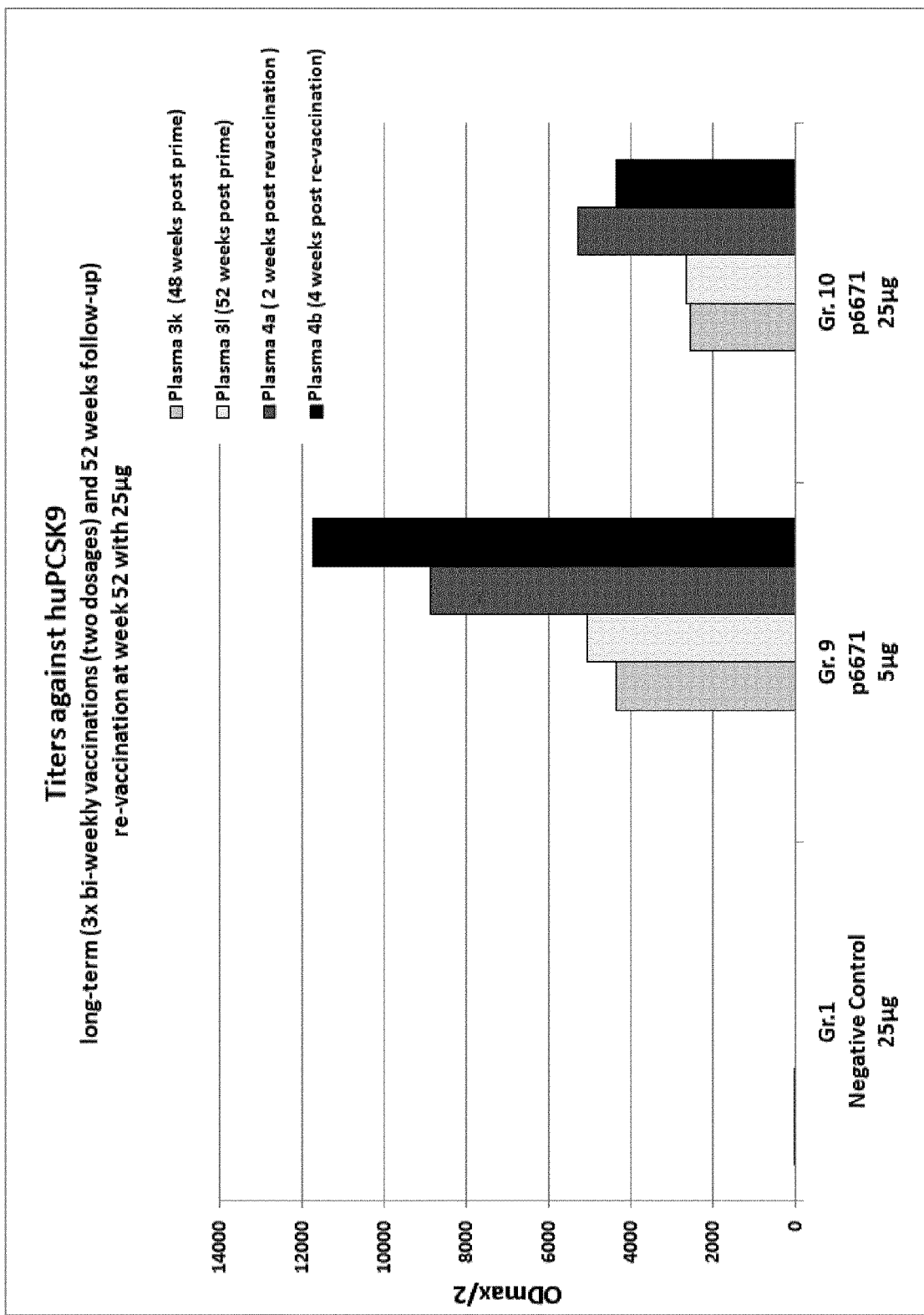

The results are shown in FIG. 3. Groups of mice received priming vaccinations at weeks 0, 2 and 4 by injecting either 5 or 25 µg AFFITOPE vaccine targeting PCSK9. Negative control mice received an irrelevant peptide coupled to KLH and adjuvanted with Alum. Abs to human PCSK9 were still detectable 48 and 52 weeks post priming for both treatment groups. However, the response was more pronounced in the group of animals that had received the lower dose. By contrast, negative control animals did not exhibit an Ab response to human PCSK9. Application of a single boost with 25 µg AFFITOPE vaccine at week 52 led to a more pronounced increase in huPCSK9 Abs, the level reached in the low dose (5 µg)/high dose (25 µg) group being about twice as high as in the high dose (25)/high dose (25) group. The single injection of 25 µg AFFITOPE vaccine did not result in an Ab response in control mice (which had not been exposed to AFFITOPE vaccine before).

Example 4

AFF008A: Successful Boosting of an Existing Immune Response Against Alpha Synuclein ("aSyn")

In the course of a clinical trial ("AFF008A"), the safety and immunological analysis of a vaccine approach based on an AFFITOPE®-based vaccine approach with an aSyn target sequence (peptide DQPVLPD; "PD01A") was analysed in patients with early stage Parkinson's Disease (PD).

PD is a common progressive neurodegenerative disorder, whose prevalence is age-correlated and affects up to 4% of people above the age of 85. The first clinical signs of the disease are movement disorders. However, non-motor symptoms like olfactory deficits, constipation, depression and orthostatic hypotension are also characteristics of disease onset while cognitive impairment to dementia might occur during disease progression. Despite an intensive scientific engagement in understanding the disease's pathogenesis, the currently available treatments are limited to symptomatic ones, but lack disease modifying properties. α-Synuclein (aSyn), and in particular its oligomeric structure, is believed to be a major pathological hallmark of disease pathogenesis, and thus is an attractive target for the development of therapies against PD.

Figures 4, 5:
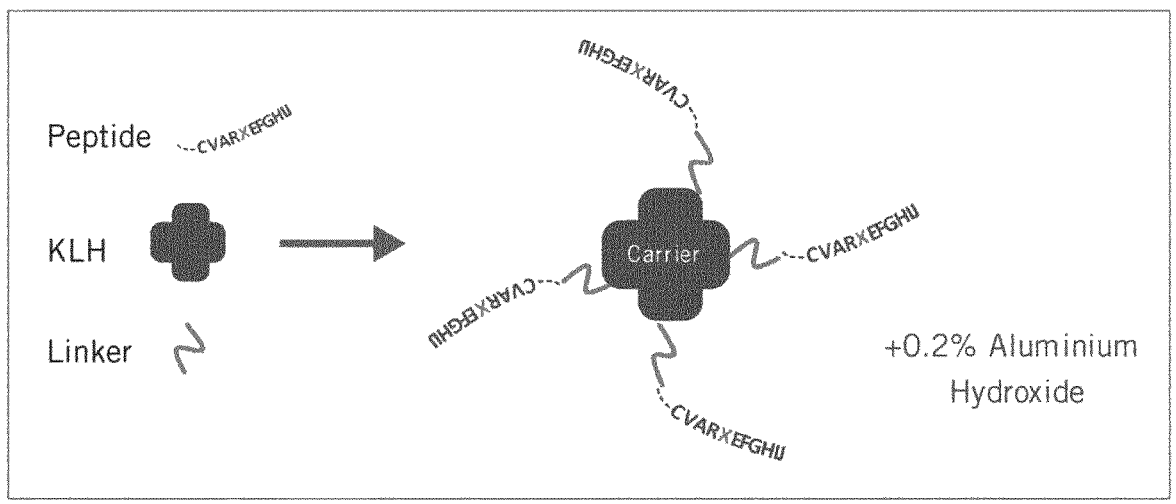
FIG. 4 shows the vaccine formulation of the AFF008A clinical trial.
FIG. 5 shows the baseline characteristics of the patients in the AFF008A clinical trial.

The aim of the present study was to develop AFFITOPE®-based vaccines (termed PD01A; FIG. 4) targeting aSyn for the long-lasting treatment or prevention of PD.

Figure 6:
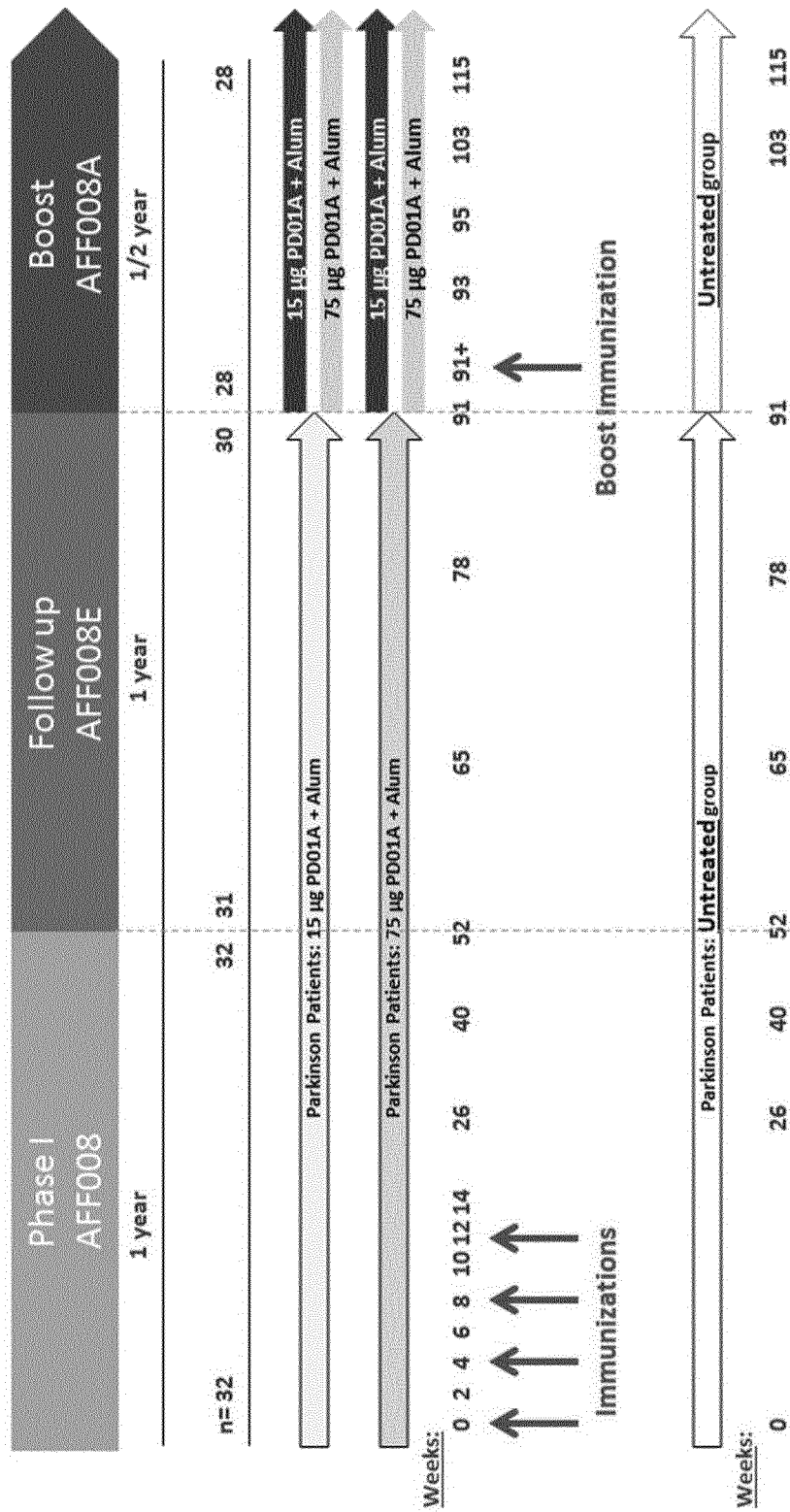
FIG. 6 shows the immunization schedule and follow-up of the AFF008A clinical trial.

Study Design and Methods:
The Phase I study AFF008A (NCT02216188—follow-up boost) to assess the immunization with the peptide-based AFFITOPE® PD01A was patient-blinded, single-centered, randomized, controlled, parallel group assessing two "boost" dosages (15 µg and 75 µg). The study was performed in early stage PD patients (FIG. 5). The primary endpoint was tolerability and safety of one s.c. boost injection (FIG. 6). Each dosage was tested in patients who had previously received four priming immunizations either with 15 µg or 75 µg AFFITOPE® PD01A (NCT01568099, "AFF008"; see example 1). Secondary endpoint was the immunological response following boosting induced by the two AFFITOPE® PD01A dosing regimens. Moreover antibody titers of IgG Abs specific for the immunization peptide, KLH (carrier protein), and aSyn target sequence were monitored by ELISA. In addition, the reactivity against aSyn recombinant protein was also measured by ELISA.

Figure 9:
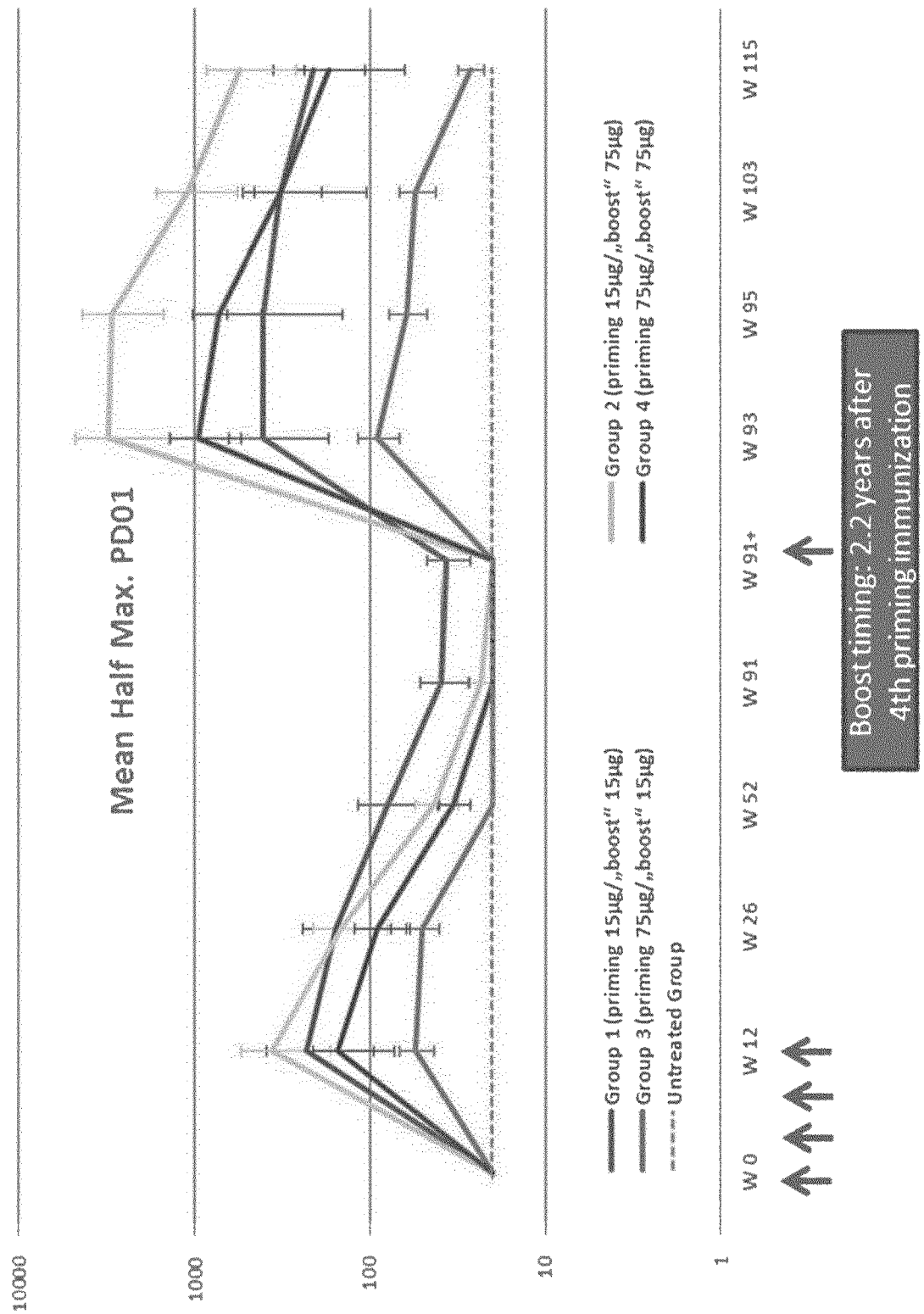
FIG. 9 shows the PD01-specific antibody titres in the AFF008A clinical trial.

Results:

The boost using two different dosages of PD01A AFFITOPE®-based vaccine was well tolerated (FIGS. 7, 8). The exploratory efficacy variables showed no deterioration of clinical symptoms in the treated groups compared to the untreated control-arm of the study. The boost vaccination with PD01A leads to the reactivation of a specific immune response appr. two years after the priming immunizations in a dose-dependent manner: PD patients immunized four times with low dose (AFF008) and boosted with high dose (AFF008A) showed a clear immunological boost. The immune response sustained throughout the entire observation period of 24 weeks (FIG. 9).

An immune response against AFFITOPE® PD01A was seen in 19 of (86%) vaccinated PD patients. 14 of these 19 PD patients (73%) generated specific antibodies against the aSyn original epitope.

CONCLUSIONS

The AFFITOPE® PD01A vaccine approach in early PD patients is well tolerated, leads to long-term immune response and is boostable.

The invention claimed is:

1. A method for vaccination against a self-antigen in a human patient wherein a dose with an effective amount of a self-antigen is administered to the patient to elicit a primary immune response, wherein the patient is subjected to a boost administration of said self-antigen, wherein the amount of the self-antigen in the dose for the boost administration is at least 50 µg and is at least 200% higher than the amount of the self-antigen in the dose used in the administration for the primary immune response, wherein the self-antigen is selected from the group consisting of proprotein convertase subtilisin/kexin type 9 (PCSK9), and an alpha synuclein antigen, and wherein the boost administration is administered at least 6 months after the first administration of the self-antigen for eliciting the primary immune response.

2. The method according to claim 1, wherein the self-antigen is an alpha synuclein antigen.

3. The method according to claim 1, wherein the self-antigen is a mimotope.

4. The method according to claim 1, wherein the boost administration is administered at least 12 months after the first administration of the self-antigen for eliciting the primary immune response.

5. The method according to claim 1, wherein the administration of the self-antigen is subcutaneous, intradermal or intramuscular administration.

6. The method according to claim 1, wherein the self-antigen is administered together with an adjuvant.

7. The method according to claim 1, wherein the self-antigen is a polypeptide comprising 7 to 30 amino acid residues and is coupled to a pharmaceutically acceptable carrier.

8. The method according to claim 1, wherein the boost administration is repeated.

9. The method according to claim 8, wherein the boost administration is repeated after at least one year and the repeated boost administration is at least 200% higher than the amount of the self-antigen in the dose used in the administration for the primary immune response.

10. The method according to claim 1, wherein the self-antigen is a polypeptide and is coupled to a pharmaceutically acceptable carrier.

* * * * *

SEQUENCE LISTING

<160> NUMBER OF SEQ ID NOS: 108

<210> SEQ ID NO 1
<211> LENGTH: 8
<212> TYPE: PRT
<213> ORGANISM: Artificial Sequence
<220> FEATURE:
<223> OTHER INFORMATION: peptide

<400> SEQUENCE: 1

Asp Met Pro Val Asp Pro Asp Asn
1               5

<210> SEQ ID NO 2
<211> LENGTH: 7
<212> TYPE: PRT
<213> ORGANISM: Artificial Sequence
<220> FEATURE:
<223> OTHER INFORMATION: peptide

<400> SEQUENCE: 2

Lys Asn Glu Glu Gly Ala Pro
1               5

<210> SEQ ID NO 3
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 3

Asp Gln Pro Val Leu Pro Asp
1               5

<210> SEQ ID NO 4
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 4

Asp Met Pro Val Leu Pro Asp
1               5

<210> SEQ ID NO 5

```
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 5

Asp Ser Pro Val Leu Pro Asp
1               5

<210> SEQ ID NO 6
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 6

Asp Ser Pro Val Trp Ala Glu
1               5

<210> SEQ ID NO 7
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 7

Asp Thr Pro Val Leu Ala Glu
1               5

<210> SEQ ID NO 8
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 8

Asp Gln Pro Val Leu Pro Asp Asn
1               5

<210> SEQ ID NO 9
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 9

Asp Met Pro Val Leu Pro Asp Asn
1               5

<210> SEQ ID NO 10
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 10

Asp Ser Pro Val Leu Pro Asp Asn
1               5

<210> SEQ ID NO 11
<211> LENGTH: 8
```

<212> TYPE: PRT
<213> ORGANISM: Artificial Sequence
<220> FEATURE:
<223> OTHER INFORMATION: alpha synuclein mimotope

<400> SEQUENCE: 11

Asp Gln Pro Val Thr Ala Glu Asn
1 5

<210> SEQ ID NO 12
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 12

Asp Ser Pro Val Trp Ala Glu Asn
1 5

<210> SEQ ID NO 13
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 13

Asp Thr Pro Val Leu Ala Glu Asn
1 5

<210> SEQ ID NO 14
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 14

His Asp Arg Pro Val Thr Pro Asp
1 5

<210> SEQ ID NO 15
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 15

Asp Arg Pro Val Thr Pro Asp
1 5

<210> SEQ ID NO 16
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 16

Asp Val Pro Val Leu Pro Asp
1 5

<210> SEQ ID NO 17
<211> LENGTH: 7
<212> TYPE: PRT

```
<213> ORGANISM: Artificial Sequence
<220> FEATURE:
<223> OTHER INFORMATION: alpha synuclein mimotope

<400> SEQUENCE: 17

Asp Thr Pro Val Tyr Pro Asp
1               5

<210> SEQ ID NO 18
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 18

Asp Thr Pro Val Ile Pro Asp
1               5

<210> SEQ ID NO 19
<211> LENGTH: 9
<212> TYPE: PRT
<213> ORGANISM: Artificial Sequence
<220> FEATURE:
<223> OTHER INFORMATION: alpha synuclein mimotope

<400> SEQUENCE: 19

His Asp Arg Pro Val Thr Pro Asp Asn
1               5

<210> SEQ ID NO 20
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 20

Asp Arg Pro Val Thr Pro Asp Asn
1               5

<210> SEQ ID NO 21
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 21

Asp Asn Pro Val His Pro Glu Asn
1               5

<210> SEQ ID NO 22
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 22

Asp Val Pro Val Leu Pro Asp Asn
1               5

<210> SEQ ID NO 23
<211> LENGTH: 8
<212> TYPE: PRT
<213> ORGANISM: Artificial Sequence
```

```
<220> FEATURE:
<223> OTHER INFORMATION: alpha synuclein mimotope

<400> SEQUENCE: 23

Asp Thr Pro Val Tyr Pro Asp Asn
1               5

<210> SEQ ID NO 24
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 24

Asp Thr Pro Val Ile Pro Asp Asn
1               5

<210> SEQ ID NO 25
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 25

Asp Gln Pro Val Leu Pro Asp Gly
1               5

<210> SEQ ID NO 26
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 26

Asp Met Pro Val Leu Pro Asp Gly
1               5

<210> SEQ ID NO 27
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 27

Asp Ser Pro Val Leu Pro Asp Gly
1               5

<210> SEQ ID NO 28
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 28

Asp Ser Pro Val Trp Ala Glu Gly
1               5

<210> SEQ ID NO 29
<211> LENGTH: 8
<212> TYPE: PRT
<213> ORGANISM: Artificial Sequence
<220> FEATURE:
```

<223> OTHER INFORMATION: alpha synuclein mimotope

<400> SEQUENCE: 29

Asp Arg Pro Val Ala Pro Glu Gly
1               5

<210> SEQ ID NO 30
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 30

Asp His Pro Val His Pro Asp Ser
1               5

<210> SEQ ID NO 31
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 31

Asp Met Pro Val Ser Pro Asp Arg
1               5

<210> SEQ ID NO 32
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 32

Asp Ser Pro Val Pro Pro Asp Asp
1               5

<210> SEQ ID NO 33
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 33

Asp Gln Pro Val Tyr Pro Asp Ile
1               5

<210> SEQ ID NO 34
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 34

Asp Arg Pro Val Tyr Pro Asp Ile
1               5

<210> SEQ ID NO 35
<211> LENGTH: 8
<212> TYPE: PRT
<213> ORGANISM: Artificial Sequence
<220> FEATURE:
<223> OTHER INFORMATION: alpha synuclein mimotope

```
<400> SEQUENCE: 35

Asp His Pro Val Thr Pro Asp Arg
1               5

<210> SEQ ID NO 36
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 36

Glu Tyr Pro Val Tyr Pro Glu Ser
1               5

<210> SEQ ID NO 37
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 37

Asp Thr Pro Val Leu Pro Asp Ser
1               5

<210> SEQ ID NO 38
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 38

Asp Met Pro Val Thr Pro Asp Thr
1               5

<210> SEQ ID NO 39
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 39

Asp Ala Pro Val Thr Pro Asp Thr
1               5

<210> SEQ ID NO 40
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 40

Asp Ser Pro Val Val Pro Asp Asn
1               5

<210> SEQ ID NO 41
<211> LENGTH: 8
<212> TYPE: PRT
<213> ORGANISM: Artificial Sequence
<220> FEATURE:
<223> OTHER INFORMATION: alpha synuclein mimotope
```

```
<400> SEQUENCE: 41

Asp Leu Pro Val Thr Pro Asp Arg
1               5

<210> SEQ ID NO 42
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 42

Asp Ser Pro Val His Pro Asp Thr
1               5

<210> SEQ ID NO 43
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 43

Asp Ala Pro Val Arg Pro Asp Ser
1               5

<210> SEQ ID NO 44
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 44

Asp Met Pro Val Trp Pro Asp Gly
1               5

<210> SEQ ID NO 45
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 45

Asp Ala Pro Val Tyr Pro Asp Gly
1               5

<210> SEQ ID NO 46
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 46

Asp Arg Pro Val Gln Pro Asp Arg
1               5

<210> SEQ ID NO 47
<211> LENGTH: 9
<212> TYPE: PRT
<213> ORGANISM: Artificial Sequence
<220> FEATURE:
<223> OTHER INFORMATION: alpha synuclein mimotope

<400> SEQUENCE: 47
```

Tyr Asp Arg Pro Val Gln Pro Asp Arg
1               5

<210> SEQ ID NO 48
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 48

Asp Met Pro Val Asp Pro Glu Asn
1               5

<210> SEQ ID NO 49
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 49

Asp Met Pro Val Asp Ala Asp Asn
1               5

<210> SEQ ID NO 50
<211> LENGTH: 8
<212> TYPE: PRT
<213> ORGANISM: Artificial Sequence
<220> FEATURE:
<223> OTHER INFORMATION: alpha synuclein mimotope

<400> SEQUENCE: 50

Glu Met Pro Val Asp Pro Asp Asn
1               5

<210> SEQ ID NO 51
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 51

Asp Asn Pro Val His Pro Glu
1               5

<210> SEQ ID NO 52
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 52

Lys Asn Asp Glu Gly Ala Pro
1               5

<210> SEQ ID NO 53
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 53

```
Ala Asn Glu Glu Gly Ala Pro
1               5

<210> SEQ ID NO 54
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 54

Lys Ala Glu Glu Gly Ala Pro
1               5

<210> SEQ ID NO 55
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 55

Lys Asn Ala Glu Gly Ala Pro
1               5

<210> SEQ ID NO 56
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 56

Arg Asn Glu Glu Gly Ala Pro
1               5

<210> SEQ ID NO 57
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 57

His Asn Glu Glu Gly Ala Pro
1               5

<210> SEQ ID NO 58
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 58

Lys Asn Glu Asp Gly Ala Pro
1               5

<210> SEQ ID NO 59
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 59

Lys Gln Glu Glu Gly Ala Pro
```

```
1               5

<210> SEQ ID NO 60
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 60

Lys Ser Glu Glu Gly Ala Pro
1               5

<210> SEQ ID NO 61
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 61

Lys Asn Asp Asp Gly Ala Pro
1               5

<210> SEQ ID NO 62
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 62

Arg Asn Asp Glu Gly Ala Pro
1               5

<210> SEQ ID NO 63
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 63

Arg Asn Glu Asp Gly Ala Pro
1               5

<210> SEQ ID NO 64
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 64

Arg Gln Glu Glu Gly Ala Pro
1               5

<210> SEQ ID NO 65
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 65

Arg Ser Glu Glu Gly Ala Pro
1               5
```

```
<210> SEQ ID NO 66
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 66

Ala Asn Asp Glu Gly Ala Pro
1               5

<210> SEQ ID NO 67
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 67

Ala Asn Glu Asp Gly Ala Pro
1               5

<210> SEQ ID NO 68
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 68

His Ser Glu Glu Gly Ala Pro
1               5

<210> SEQ ID NO 69
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 69

Ala Ser Glu Glu Gly Ala Pro
1               5

<210> SEQ ID NO 70
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 70

His Asn Glu Asp Gly Ala Pro
1               5

<210> SEQ ID NO 71
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 71

His Asn Asp Glu Gly Ala Pro
1               5
```

```
<210> SEQ ID NO 72
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 72

Arg Asn Ala Glu Gly Ala Pro
1               5

<210> SEQ ID NO 73
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 73

His Asn Ala Glu Gly Ala Pro
1               5

<210> SEQ ID NO 74
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 74

Lys Ser Ala Glu Gly Ala Pro
1               5

<210> SEQ ID NO 75
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 75

Lys Ser Asp Glu Gly Ala Pro
1               5

<210> SEQ ID NO 76
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 76

Lys Ser Glu Asp Gly Ala Pro
1               5

<210> SEQ ID NO 77
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 77

Arg Gln Asp Glu Gly Ala Pro
1               5
```

```
<210> SEQ ID NO 78
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 78

Arg Gln Glu Asp Gly Ala Pro
1               5

<210> SEQ ID NO 79
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 79

His Ser Ala Glu Gly Ala Pro
1               5

<210> SEQ ID NO 80
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 80

Arg Ser Ala Glu Gly Ala Pro
1               5

<210> SEQ ID NO 81
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 81

Arg Ser Asp Glu Gly Ala Pro
1               5

<210> SEQ ID NO 82
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 82

Arg Ser Glu Asp Gly Ala Pro
1               5

<210> SEQ ID NO 83
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 83

His Ser Asp Glu Gly Ala Pro
1               5

<210> SEQ ID NO 84
```

```
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 84

His Ser Glu Asp Gly Ala Pro
1               5

<210> SEQ ID NO 85
<211> LENGTH: 7
<212> TYPE: PRT
<213> ORGANISM: Artificial Sequence
<220> FEATURE:
<223> OTHER INFORMATION: alpha synuclein mimotope

<400> SEQUENCE: 85

Arg Gln Asp Asp Gly Ala Pro
1               5

<210> SEQ ID NO 86
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 86

Asp Pro Val Tyr Ile His Pro Phe
1               5

<210> SEQ ID NO 87
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 87

Asp Ala Val Tyr Ile His Pro Phe
1               5

<210> SEQ ID NO 88
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 88

Asp Arg His Tyr Ile His Pro Phe
1               5

<210> SEQ ID NO 89
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 89

Asp Ala Ala Tyr Ile His Pro Phe
1               5

<210> SEQ ID NO 90
<211> LENGTH: 8
```

<212> TYPE: PRT
<213> ORGANISM: Artificial Sequence
<220> FEATURE:
<223> OTHER INFORMATION: angiotensin II mimotope

<400> SEQUENCE: 90

Asp Arg Ala Tyr Ala His Pro Phe
1               5

<210> SEQ ID NO 91
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 91

Asp Pro Gly Tyr Ile His Pro Phe
1               5

<210> SEQ ID NO 92
<211> LENGTH: 8
<212> TYPE: PRT
<213> ORGANISM: Artificial Sequence
<220> FEATURE:
<223> OTHER INFORMATION: angiotensin II mimotope

<400> SEQUENCE: 92

Asp Arg Ala Tyr Asp His Pro Phe
1               5

<210> SEQ ID NO 93
<211> LENGTH: 7
<212> TYPE: PRT
<213> ORGANISM: Artificial Sequence
<220> FEATURE:
<223> OTHER INFORMATION: angiotensin II mimotope

<400> SEQUENCE: 93

Ala Ala Tyr Ile His Pro Phe
1               5

<210> SEQ ID NO 94
<211> LENGTH: 7
<212> TYPE: PRT
<213> ORGANISM: Artificial Sequence
<220> FEATURE:
<223> OTHER INFORMATION: angiotensin II mimotope

<400> SEQUENCE: 94

Arg Ala Tyr Ala His Pro Phe
1               5

<210> SEQ ID NO 95
<211> LENGTH: 7
<212> TYPE: PRT
<213> ORGANISM: Artificial Sequence
<220> FEATURE:
<223> OTHER INFORMATION: angiotensin II mimotope

<400> SEQUENCE: 95

Pro Gly Tyr Ile His Pro Phe
1               5

<210> SEQ ID NO 96
<211> LENGTH: 10
<212> TYPE: PRT

```
<213> ORGANISM: Artificial Sequence
<220> FEATURE:
<223> OTHER INFORMATION: PCSK9 mimotope

<400> SEQUENCE: 96

Ser Ile Pro Trp Ser Leu Glu Arg Ile Thr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 97

Ser Ile Pro Trp Ser Leu Glu Arg Ile Thr Pro Pro Arg
1               5                   10

<210> SEQ ID NO 98
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 98

Ser Ile Pro Trp Ser Leu Glu Arg Thr Thr Pro Pro Arg
1               5                   10

<210> SEQ ID NO 99
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 99

Val Ile Pro Trp Asn Leu Glu Arg Ile Leu Pro Pro Arg
1               5                   10

<210> SEQ ID NO 100
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 100

Ser Val Pro Trp Asn Leu Glu Arg Ile Gln Pro Pro Arg
1               5                   10

<210> SEQ ID NO 101
<211> LENGTH: 10
<212> TYPE: PRT
<213> ORGANISM: Artificial Sequence
<220> FEATURE:
<223> OTHER INFORMATION: PCSK9 mimotope

<400> SEQUENCE: 101

Ser Ile Pro Trp Ser Leu Glu Arg Thr Thr
1               5                   10

<210> SEQ ID NO 102
<211> LENGTH: 10
<212> TYPE: PRT
<213> ORGANISM: Artificial Sequence
```

```
<220> FEATURE:
<223> OTHER INFORMATION: PCSK9 mimotope

<400> SEQUENCE: 102

Ser Ile Pro Trp Ser Leu Glu Arg Leu Thr
1               5                   10

<210> SEQ ID NO 103
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 103

Ser Ile Pro Trp Ser Leu Glu Arg Leu Thr Pro Pro Arg
1               5                   10

<210> SEQ ID NO 104
<211> LENGTH: 10
<212> TYPE: PRT
<213> ORGANISM: Artificial Sequence
<220> FEATURE:
<223> OTHER INFORMATION: PCSK9 mimotope

<400> SEQUENCE: 104

Ser Ile Pro Trp Ser Leu Glu Arg Ile Gln
1               5                   10

<210> SEQ ID NO 105
<211> LENGTH: 13
<212> TYPE: PRT
<213> ORGANISM: Artificial Sequence
<220> FEATURE:
<223> OTHER INFORMATION: PCSK9 mimotope

<400> SEQUENCE: 105

Ser Ile Pro Trp Ser Leu Glu Arg Ile Gln Pro Pro Arg
1               5                   10

<210> SEQ ID NO 106
<211> LENGTH: 10
<212> TYPE: PRT
<213> ORGANISM: Artificial Sequence
<220> FEATURE:
<223> OTHER INFORMATION: PCSK9 mimotope

<400> SEQUENCE: 106

Val Ile Pro Trp Asn Leu Glu Arg Ile Leu
1               5                   10

<210> SEQ ID NO 107
<211> LENGTH: 10
<212> TYPE: PRT
<213> ORGANISM: Artificial Sequence
<220> FEATURE:
<223> OTHER INFORMATION: PCSK9 mimotope

<400> SEQUENCE: 107

Ser Val Pro Trp Asn Leu Glu Arg Ile Gln
1               5                   10

<210> SEQ ID NO 108
<211> LENGTH: 7
<212> TYPE: PRT
<213> ORGANISM: Artificial Sequence
<220> FEATURE:
```

```
<223> OTHER INFORMATION: alpha synuclein mimotope

<400> SEQUENCE: 108

Arg Gln Asp Glu Gly Ala Pro
1               5
```